(12) United States Patent
Thompson et al.

(10) Patent No.: US 7,846,723 B2
(45) Date of Patent: Dec. 7, 2010

(54) METHODS OF IDENTIFYING ANTI-CANCER AGENTS AND USES THEREOF

(75) Inventors: Craig B Thompson, Merion Station, PA (US); Wei-Xing Zong, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/211,046

(22) Filed: Sep. 15, 2008

(65) Prior Publication Data

US 2009/0093458 A1 Apr. 9, 2009

Related U.S. Application Data

(62) Division of application No. 11/013,574, filed on Dec. 15, 2004, now Pat. No. 7,439,031.

(60) Provisional application No. 60/529,642, filed on Dec. 15, 2003.

(51) Int. Cl.
*C12N 5/00* (2006.01)
(52) U.S. Cl. .................... 435/325; 435/810
(58) Field of Classification Search ............... None
See application file for complete search history.

(56) References Cited

U.S. PATENT DOCUMENTS 7,247,700 B2 * 7/2007 Korsmeyer et al. .......... 530/300
2003/0091982 A1 * 5/2003 Zong et al. .................. 435/4

OTHER PUBLICATIONS

Wei et al (Science, 2001, 292:727-730, IDS).*
Zong et al (J of Cell Biology, Jul. 7, 2003, 162:59-69, IDS).*
Ochs et al (Cancer Research, 2000, 60:5815-5824).*
Lindsten et al (J of Neoruscience, Dec. 3, 2003, 23:11112-11119).*
Scorrano et al (Science, Apr. 2003, 300:135-139, IDS).*
Adams, J.M. 2003. Ways of dying: multiple pathways to apoptosis. Genes Dev 17: 2481-95.
Baggetto, L.G. 1992. Deviant energetic metabolism of glycolytic cancer cells. Biochimie 74: 959-74.
Burkart, V., Z.Q. Wang, J. Radons, B. Heller, Z. Herceg, L. Stingl, E.F. Wagner, and H. Kolb. 1999. Mice lacking the poly(ADP-ribose) polymerase gene are resistant to pancreatic beta-cell destruction and diabetes development induced by streptozocin. Nat Med 5: 314-9.
Butler, A.P., J.K. Mardian, and D.E. Olins. 1985. Nonhistone chromosomal protein HMG 1 interactions with DNA. Fluorescence and thermal denaturation studies. J Biol Chem 260: 10613-20.
Chabruer, B.A. and D.L. Longo. 2001. Cancer Chemotherapy and Biotherapy: Principles and Practices. In. Lippincott Williams and Wilkins, Philadelphia.
Cheng, E.H., M.C. Wei, S. Weiler, R.A. Flavell, T.W. Mak, T. Lindsten, and S.J. Korsmeyer. 2001. BCL-2, BCL-X(L) sequester BH3 domain-only molecules preventing BAX- and BAK-mediated mitochondrial apoptosis. Mol Cell 8: 705-11.

D'Amours, D., S. Desnoyers, I. D'Silva, and G.G. Poirier. 1999. Poly(ADP-ribosyl)ation reactions in the regulation of nuclear functions. Biochem J 342 ( Pt 2): 249-68.
Degenhardt, K., G. Chen, T. Lindsten, and E. White. 2002a. BAX and BAK mediate p53- independent suppression of tumorigenesis. Cancer Cell 2: 193-203.
Degenhardt, K., R. Sundararajan, T. Lindsten, C. Thompson, and E. White. 2002b. Bax and Bak independently promote cytochrome C release from mitochondria. J Biol Chem 277: 14127-34.
DeVita, V.T. 1997. Principles of Cancer Management: Chemotherapy. In Cancer: Principles and Practice of Oncology (ed. V.T. DeVita, S. Hellman, and S.A. Rosenberg), pp. 333-347. Lippincott-Raven, Philadelphia.
Eaton, S., K. Bartlett, and M. Pourfarzam. 1996. Mammalian mitochondrial beta-oxidation. Biochem J 320 ( Pt 2): 345-57.
Eliasson, M.J., K. Sampei, A.S. Mandir, P.D. Hum, R.J. Traystman, J. Bao, A. Pieper, Z.Q. Wang, T.M. Dawson, S.H. Snyder, and V.L. Dawson. 1997. Poly(ADP-ribose) polymerase gene disruption renders mice resistant to cerebral ischemia. Nat Med 3: 1089-95.
Evan, G.I. and K.H. Vousden. 2001. Proliferation, cell cycle and apoptosis in cancer. Nature 411: 342-8.
Gonin-Giraud, S., A.L. Mathieu, S. Diocou, M. Tomkowiak, G. Delorme, and J. Marvel. 2002. Decreased glycolytic metabolism contributes to but is not the inducer of apoptosis following IL-3-starvation. Cell Death Differ 9: 1147-57.
Gudkov, A.V. and E.A. Komarova. 2003. The role of p53 in determining sensitivity to radiotherapy. Nat Rev Cancer 3: 117-29.
Ha, H.C. and S.H. Snyder. 1999. Poly(ADP-ribose) polymerase is a mediator of necrotic cell death by ATP depletion. Proc Natl Acad Sci U S A 96: 13978-82.
Hartley, A., J.M. Stone, C. Heron, J.M. Cooper, and A.H. Schapira. 1994. Complex I inhibitors induce dose-dependent apoptosis in PC12 cells: relevance to Parkinson's disease. J Neurochem 63: 1987-90.
Holt, J.A. 1983. Cancer, a disease of defective glucose metabolism. Med Hypotheses 10: 133-50.
Jacobson, E.L. and M.K. Jacobson. 1976. Pyridine nucleotide levels as a function of growth in normal and transformed 3T3 cells. Arch Biochem Biophys 175: 627-34.
Kanduc, D., A. Mittelman, R. Serpico, E. Sinigaglia, A.A. Sinha, C. Natale, R. Santacroce, M.G. Di Corcia, A. Lucchese, L. Dini, P. Pani, S. Santacroce, S. Simone, R. Bucci, and E. Farber. 2002. Cell death: apoptosis versus necrosis (review). Int J Oncol 21: 165-70.

(Continued)

*Primary Examiner*—Laura B Goddard
(74) *Attorney, Agent, or Firm*—Pepper Hamilton LLP

(57) ABSTRACT

The present invention provides methods of identifying and/or detecting anti-cancer agents. The present invention provides methods of identifying and/or detecting compounds that can activate PARP and/or induce necrosis. The present invention also provides for methods of treating cancer in an individual. The present invention also provides kits for identifying and/or detecting anti-cancer agents.

9 Claims, 10 Drawing Sheets

OTHER PUBLICATIONS

Liang, Y., C. Buettger, D.K. Berner, and F.M. Matschinsky. 1997. Chronic effect of fatty acids on insulin release is not through the alteration of glucose metabolism in a pancreatic beta-cell line (beta HC9). Diabetologia 40: 1018-27.

Lindsten, T., A.J. Ross, A. King, W.X. Zong, J.C. Rathmell, H.A. Shiels, E. Ulrich, K.G. Waymire, P. Mahar, K. Frauwirth, Y. Chen, M. Wei, V.M. Eng, D.M. Adelman, M.C. Simon, A. Ma, J.A. Golden, G. Evan, S.J. Korsmeyer, G.R. MacGregor, and C.B. Thompson. 2000. The combined functions of proapoptotic Bcl-2 family members bak and bax are essential for normal development of multiple tissues. Mol Cell 6: 1389-99.

Lister, T.A. 1991. The management of follicular lymphoma. Ann Oncol 2 Suppl 2: 131-5.

Majno, G. and I. Joris. 1995. Apoptosis, oncosis, and necrosis. An overview of cell death. Am J Pathol 146: 3-15.

Masutani, M., H. Suzuki, N. Kamada, M. Watanabe, O. Ueda, T. Nozaki, K. Jishage, T. Watanabe, T. Sugimoto, T. Nakagama, T. Ochiya, and T. Sugimura. 1999. Poly(ADP-ribose) polymerase gene disruption conferred mice resistant to streptozotocin-induced diabetes. Proc Natl Acad Sci U S A 96: 2301-4.

Muller, S., P. Scaffidi, B. Degryse, T. Bonaldi, L. Ronfani, A. Agresti, M. Beltrame, and M.E. Bianchi. 2001. New EMBO members' review: the double life of HMGB1 chromatin protein: architectural factor and extracellular signal. Embo J 20: 4337-40.

Myung, P.S., J.L. Clements, D.W. White, Z.A. Malik, J.S. Cowdery, L.H. Allen, J.T. Harty, D.J. Kusner, and G.A. Koretzky. 2000. In vitro and in vivo macrophage function can occur independently of SLP-76. Int Immunol 12: 887-97.

Ohgoh, M., H. Shimizu, H. Ogura, and Y. Nishizawa. 2000. Astroglial trophic support and neuronal cell death: influence of cellular energy level on type of cell death induced by mitochondrial toxin in cultured rat cortical neurons. J Neurochem 75: 925-33.

Pieper, A.A., D.J. Brat, D.K. Krug, C.C. Watkins, A. Gupta, S. Blackshaw, A. Verma, Z.Q. Wang, and S.H. Snyder. 1999a. Poly(ADP-ribose) polymerase-deficient mice are protected from streptozotocin-induced diabetes. Proc Natl Acad Sci U S A 96: 3059-64.

Pieper, A.A., A. Verma, J. Zhang, and S.H. Snyder. 1999b. Poly (ADP-ribose) polymerase, nitric oxide and cell death. Trends Pharmacol Sci 20: 171-81.

Scaffidi, P., T. Misteli, and M.E. Bianchi. 2002. Release of chromatin protein HMGB1 by necrotic cells triggers inflammation. Nature 418: 191-5.

Scorrano, L., S.A. Oakes, J.T. Opferman, E.H. Cheng, M.D. Sorcinelli, T. Pozzan, and S.J. Korsmeyer. 2003. BAX and BAK regulation of endoplasmic reticulum Ca2+: a control point for apoptosis. Science 300: 135-9.

Shchepina, L.A., E.N. Popova, O.Y. Pletjushkina, and B.V. Chemyak. 2002. Respiration and mitochondrial membrane potential are not required for apoptosis and anti-apoptotic action of Bcl-2 in HeLa cells. Biochemistry (Mosc) 67: 222-6.

Smith, S. 2001. The world according to PARP. Trends Biochem Sci 26: 174-9.

Szabo, C. and V.L. Dawson. 1998. Role of poly(ADP-ribose) synthetase in inflammation and ischaemia-reperfusion. Trends Pharmacol Sci 19: 287-98.

Szabo, C., B. Zingarelli, M. O'Connor, and A.L. Salzman. 1996. DNA strand breakage, activation of poly (ADP-ribose) synthetase, and cellular energy depletion are involved in the cytotoxicity of macrophages and smooth muscle cells exposed to peroxynitrite. Proc Natl Acad Sci U S A 93: 1753-8.

Tsujimoto, Y., L.R. Finger, J. Yunis, P.C. Nowell, and C.M. Croce. 1984. Cloning of the chromosome breakpoint of neoplastic B cells with the t(14;18) chromosome translocation. Science 226: 1097-9.

Vander Heiden, M.G., N.S. Chandel, P.T. Schumacker, and C.B. Thompson. 1999. Bcl-xL prevents cell death following growth factor withdrawal by facilitating mitochondrial ATP/ADP exchange. Mol Cell 3: 159-67.

Vousden, K.H. and X. Lu. 2002. Live or let die: the cell's response to p53. Nat Rev Cancer 2: 594-604.

Wang, X. 2001. The expanding role of mitochondria in apoptosis. Genes Dev 15: 2922-33.

Wang, Z.Q., B. Auer, L. Stingl, H. Berghammer, D. Haidacher, M. Schweiger, and E.F. Wagner. 1995. Mice lacking ADPRT and poly(ADP-ribosyl)ation develop normally but are susceptible to skin disease. Genes Dev 9: 509-20.

Wang, Z.Q., L. Stingl, C. Morrison, M. Jantsch, M. Los, K. Schulze-Osthoff, and E.F. Wagner. 1997. PARP is important for genomic stability but dispensable in apoptosis. Genes Dev 11: 2347-58.

Wei, M.C., W.X. Zong, E.H. Cheng, T. Lindsten, V. Panoutsakopoulou, A.J. Ross, K.A. Roth, G.R. MacGregor, C.B. Thompson, and S.J. Korsmeyer. 2001. Proapoptotic BAX and BAK: a requisite gateway to mitochondrial dysfunction and death. Science 292: 727-30.

Woodgate, A., G. MacGibbon, M. Walton, and M. Dragunow. 1999. The toxicity of 6-hydroxydopamine on PC12 and P19 cells. Brain Res Mol Brain Res 69: 84-92.

Yu, S.W., H. Wang, M.F. Poitras, C. Coombs, W.J. Bowers, H.J. Federoff, G.G. Poirier, T.M. Dawson, and V.L. Dawson. 2002. Mediation of poly(ADP-ribose) polymerase-1-dependent cell death by apoptosis-inducing factor. Science 297: 259-63.

Zong, W.X., C. Li, G. Hatzivassiliou, T. Lindsten, Q.C. Yu, J. Yuan, and C.B. Thompson. 2003. Bax and Bak can localize to the endoplasmic reticulum to initiate apoptosis. J Cell Biol 162: 59-69.

Zong, W.X., T. Lindsten, A.J. Ross, G.R. MacGregor, and C.B. Thompson. 2001. BH3-only proteins that bind pro-survival Bcl-2 family members fail to induce apoptosis in the absence of Bax and Bak. Genes Dev 15: 1481-6.

Zips et al., 2005, In Vivo, 19:1-7.

Freshney, Culture of Animal Cells, A Manual of Basic Technique, Alan R. Liss, Inc., 1983, New York, p. 4.

Dermer, 1994, Biotechnology, 12:320.

Hampton et al. FEBS Letters, 1997, 414:552-556.

Leist et al., J. Exp. Med, 1997, 185:1481-1486.

Herceg et al. Molecular and Cellular Biology, 1999, 19:5124-5133.

Szabo et al., Nitric Oxide, 1997, 1:373-385.

Szabo, Free Radical Biology & Medicine, 1996, 21:855-896.

Bakondi et al. J of Histochemistry & Cytochemistry, 2002, 50:91-98.

The American Cancer Society Journal CA, A Cancer Journal for Clinicians, 1993, 43:47-56.

Casenghi et al., Exp. Cell. Res. 1999, 250:399-50, abstract only.

Korbelik et al., Photochemistry and Photobiology, 1993, 78:400-406.

Soldani et al., Experimental Cell Research, 2001, 269:193-201.

* cited by examiner

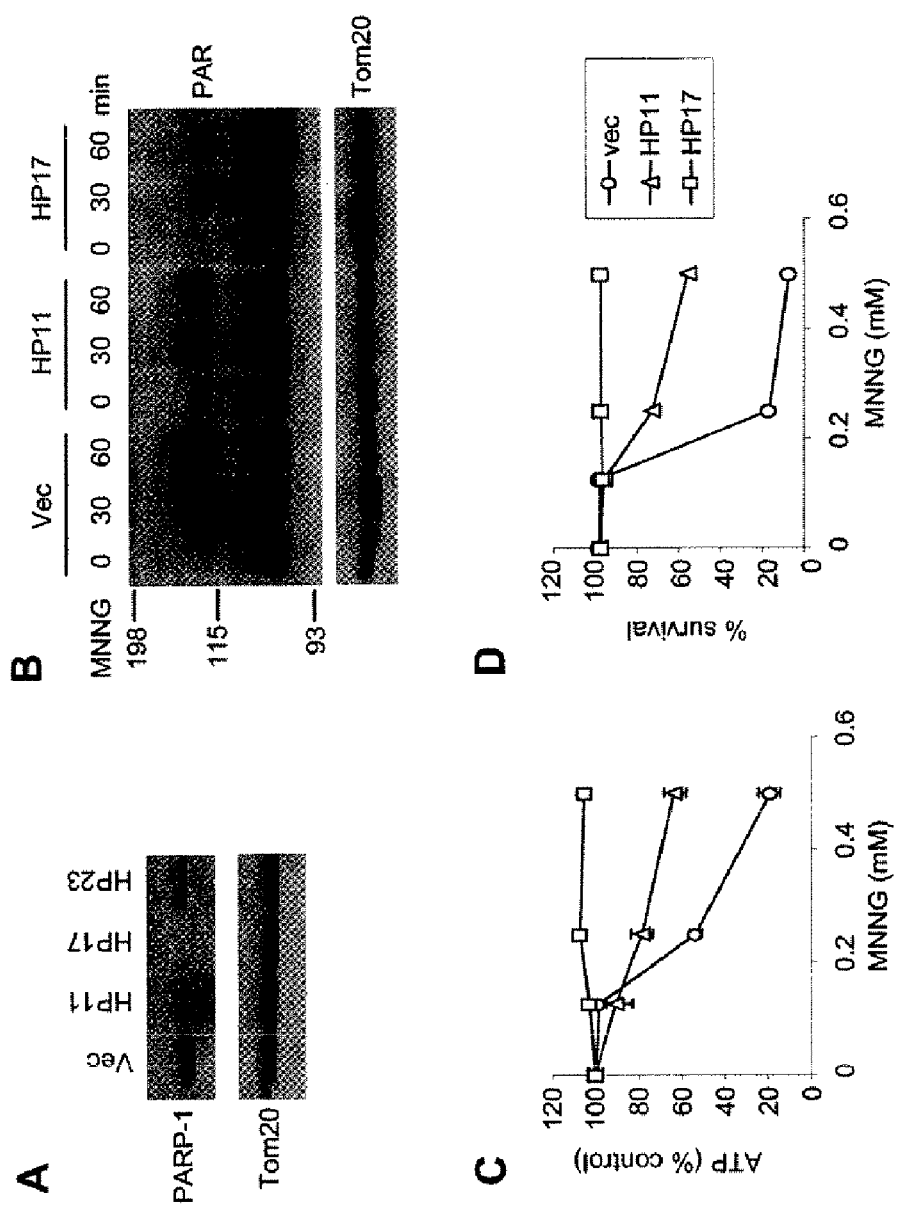
FIGURE 3, PANELS A-D

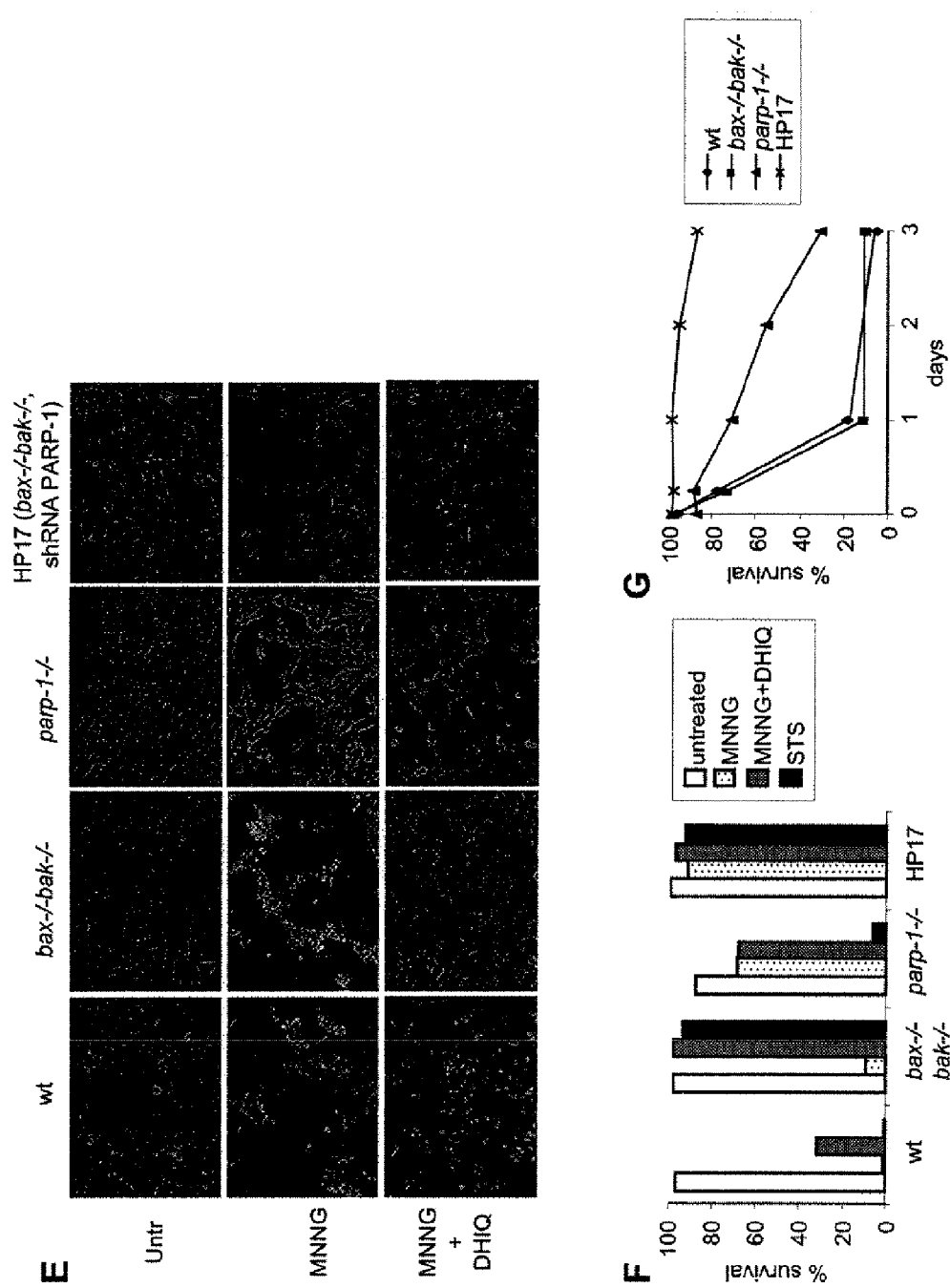
FIGURE 3, PANELS E-G

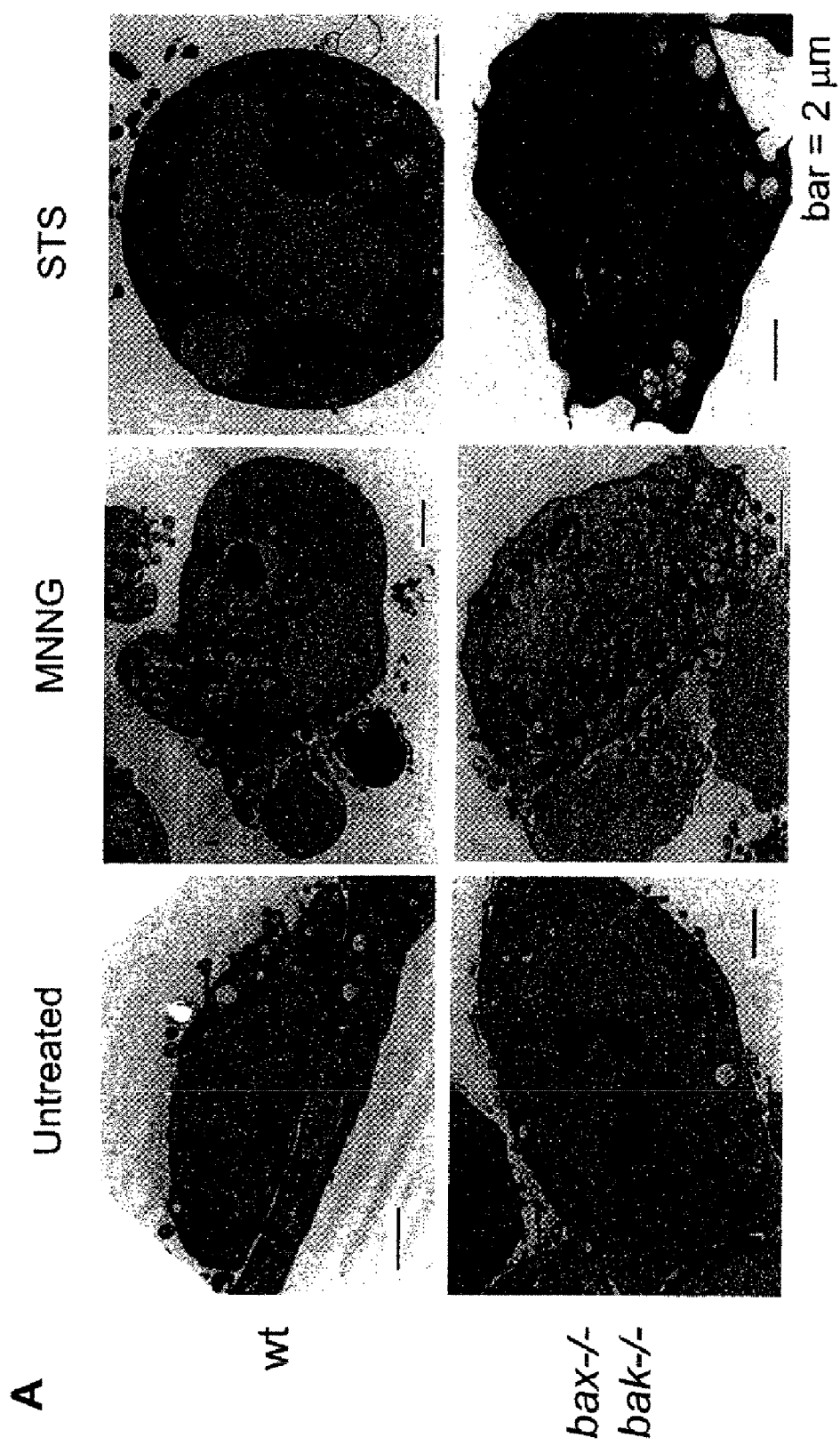
FIGURE 4, PANEL A

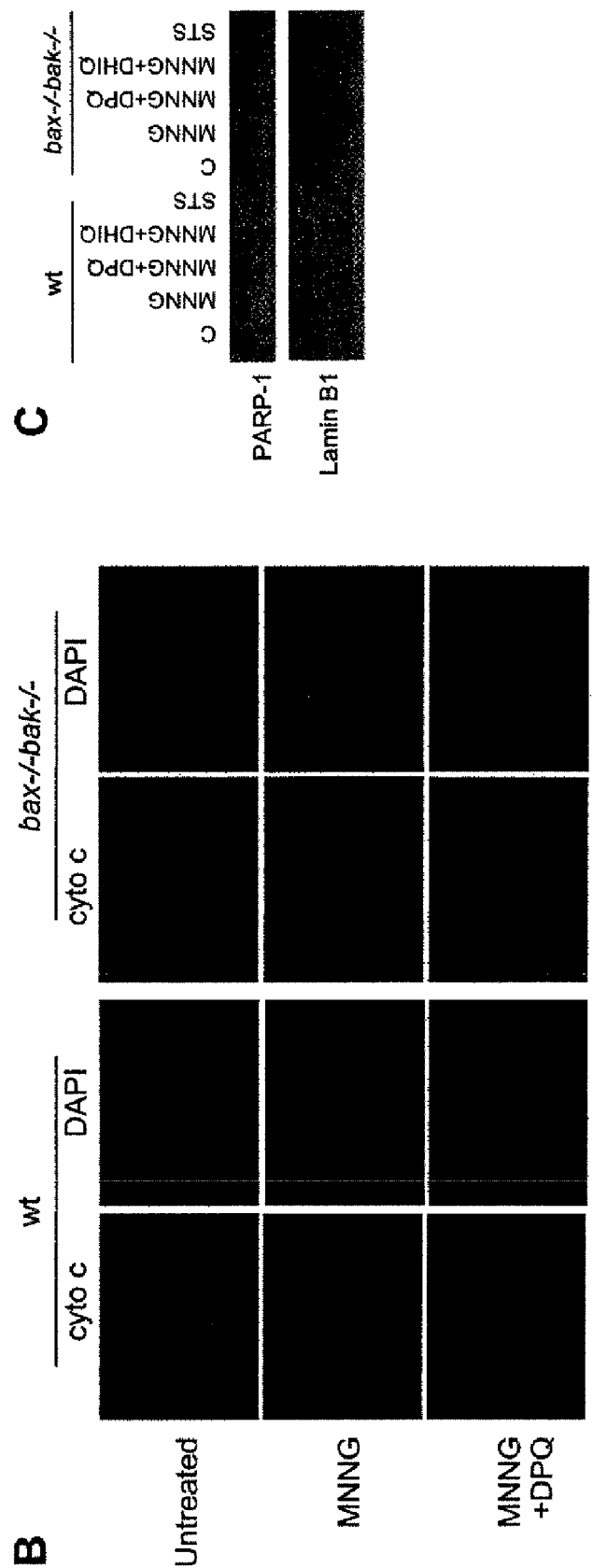
FIGURE 4, PANELS B-C

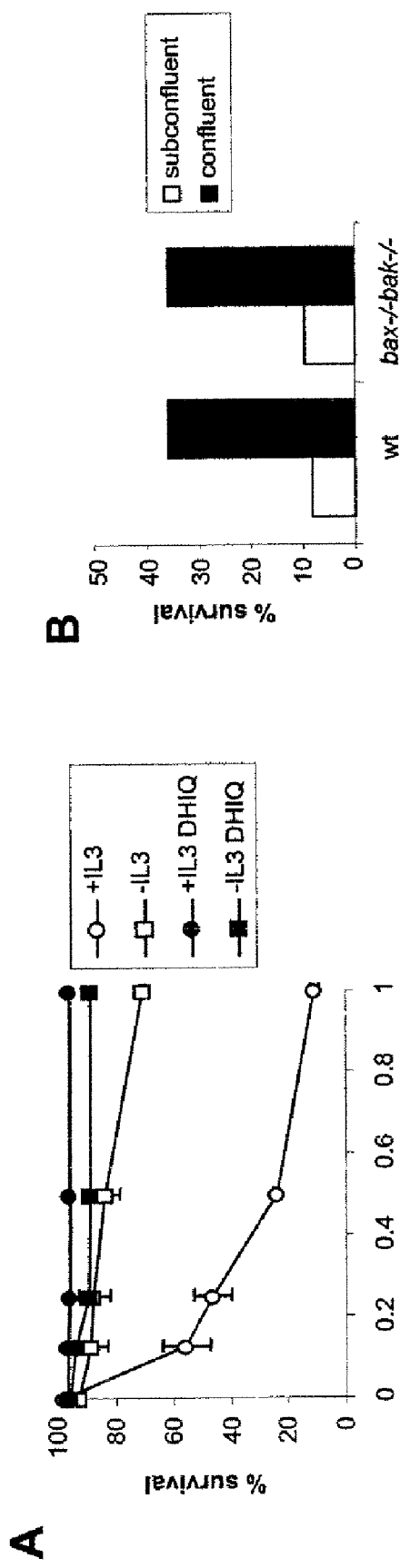
FIGURE 6, PANELS A-B

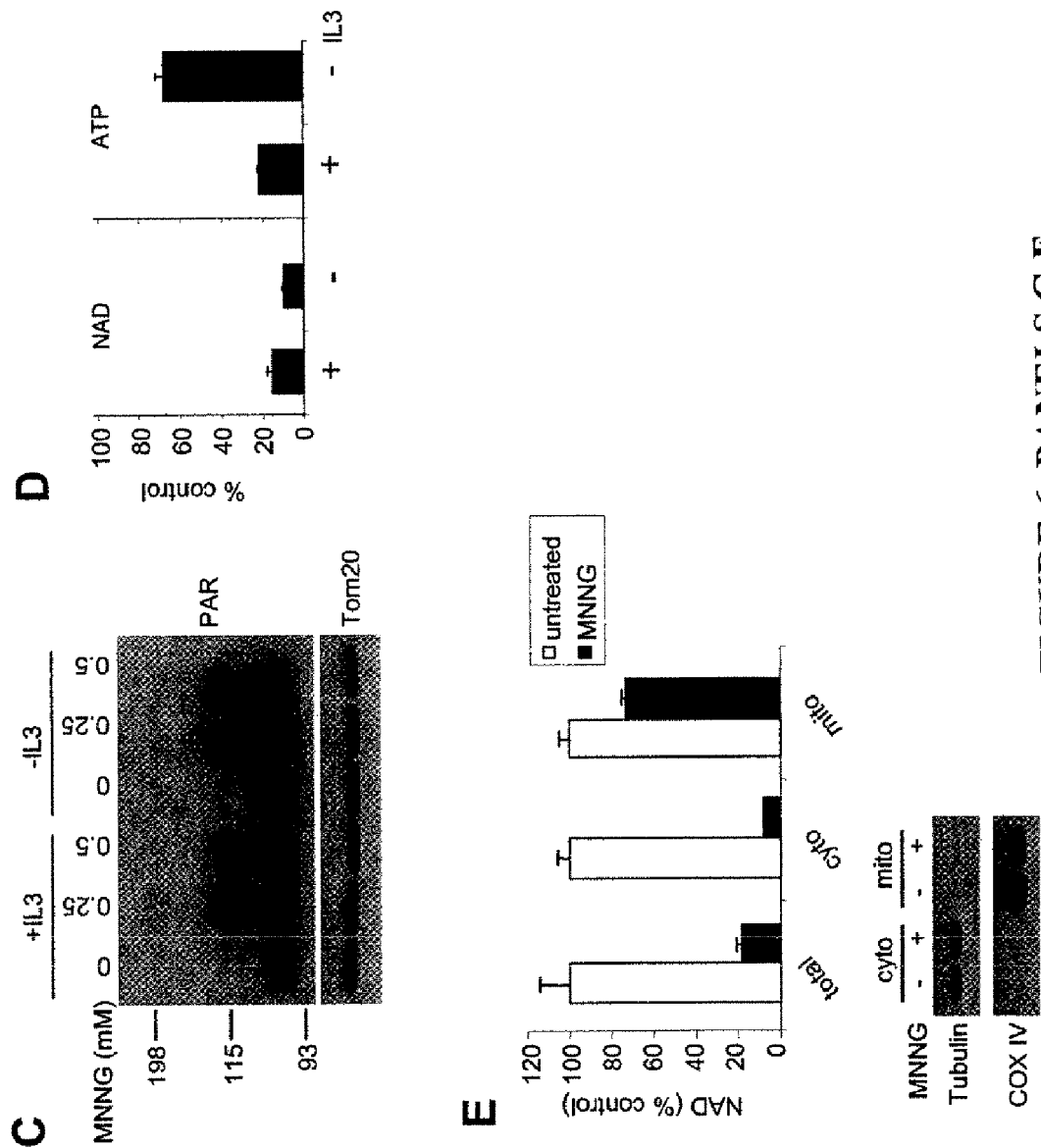
FIGURE 6, PANELS C-E

SEQUENCE LISTING

```
<160> NUMBER OF SEQ ID NOS: 2

<210> SEQ ID NO 1
<211> LENGTH: 21
<212> TYPE: DNA
<213> ORGANISM: Homo sapiens

<400> SEQUENCE: 1
cagtggaaag acgcgcaggc a                                             21

<210> SEQ ID NO 2
<211> LENGTH: 78
<212> TYPE: DNA
<213> ORGANISM: Homo sapiens

<400> SEQUENCE: 2
aaaaaaggaa gtgaaagcgg ccaacgttcc tcgagcaacg ttggccgctt tcacttccgt    60
gtttcgtcct ttccacaa                                                 78
```

METHODS OF IDENTIFYING ANTI-CANCER AGENTS AND USES THEREOF

CROSS-REFERENCE TO RELATED APPLICATIONS

This application claims priority to U.S. Non-Provisional application Ser. No. 11/013,574, which issued as U.S. Pat. No. 7,439,031, which claims priority to U.S. Provisional Application Ser. No. 60/529,642, filed Dec. 15, 2003, all of which are incorporated herein by reference in its entirety.

BACKGROUND OF THE INVENTION

Cell death plays an important role in development, tissue homeostasis, and degenerative diseases. Two major forms of cell death have been described: apoptosis and necrosis. Apoptosis, also called programmed cell death, is an energy-driven process by which a ceil actively destroys itself in response to extracellular signals or developmental cues, whereas necrosis has been considered a passive process in which a cell dies as a result of bioenergetic catastrophe. Apoptosis is characterized by the ordered cellular degradation of proteins and organelles, maintenance of plasma membrane integrity, and non-inflammatory phagocytosis of the dying cell (Adams 2003; Wang 2001). During necrosis, cells swell rapidly and lose the integrity of their plasma membrane, releasing cellular contents into the extracellular environment, and triggering an acute inflammatory response. Necrosis has traditionally been considered an unregulated form of cell death, and has been well characterized in a wide range of pathologic states including ischemia, trauma, and infection (Majno and Joris 1995; Kanduc et al. 2002).

A great deal of recent attention has focused on the role of apoptosis in normal development and various disease processes. Most if not all cancer cells have defects in the normal control of apoptosis. The first characterized example of this is the 14:18 chromosomal translocation found in patients with follicular lymphoma that juxtaposes the immunoglobulin enhancer with the anti-apoptotic gene bcl-2 (Tsujimoto et al. 1984). Enhanced expression of Bcl-2 provides resistance to apoptosis by suppressing the activation of the proapoptotic Bcl-2 related proteins Bax and flak. Bax and Bak are essential in apoptosis initiated from both mitochondria and the endoplasmic reticulum (ER). Cells lacking both Bax and Bak are resistant to apoptosis induced by developmental cues, signal transduction through death receptors, growth factor withdrawal, and ER stress (Lindsten et al. 2000; Wei et al. 2001; Zong et al. 2001, Cheng et al. 2001; Degenhardt et al. 2002b; Scorrano et al. 2003; Zong et al. 2003).

Despite the role of Bcl-2 as an anti-apoptotic protein, follicular lymphoma cells are sensitive to treatment with DNA alkylating drugs in vivo (Lister 1991).

Although there have been advancements in the treatment of cancer a hallmark of many cancers is that the treatments fail to work after a period of time as the cancer cells become resistant to the treatment. Much of this resistance is due to inhibition of the apoptosis pathway due to genetic mutations in the cell. However, cells can still die by other processes including necrosis. Thus, there is a need to identify compounds that can act as anti-cancer agents. There is also a need to identify anti-cancer agents that are able to kill cancer cells that do not die by apoptosis.

SUMMARY OF THE INVENTION

In some embodiments, the present invention provides methods of detecting an anti-cancer agent comprising performing a test assay comprising contacting an immortalized cell with a test compound and measuring PARP activity.

In some embodiments, the present invention provides kits for identifying a PARP activator comprising In some embodiments, the present invention provides methods of treating cancer in an individual comprising identifying an anti-cancer agent and administering the agent to the individual.

BRIEF DESCRIPTION OF DRAWINGS

FIG. 3, Panels A-G, show that PARP inhibition results in resistance to MNNG-induced cell death. Panel A: PARP-1 shRNA in bax$^{-/-}$bak$^{-/-}$ cells. Stable clones were selected from bax$^{-/-}$ bak$^{-/-}$ MEFs transfected with vector or PARP-1 hairpins. Cell lysates were made from vector cell line or PARP-1 hairpin cell lines. Immunoblotting was performed using an anti-PARP-1 antibody, and an anti-Tom20 antibody as a control for equal loading. Note that PARP-1 expression was suppressed significantly in Clone HP17, moderately in HP11, and not effected in HP23. Panel B: PARP activity was determined using triplicate samples by immunoblotting using an anti-PAR antibody. Panel C: ATP levels were measured after 30 min treatment with MNNG at indicated concentrations. Panel D: Cell survival was determined by PI exclusion 20 h after MNNG treatment. Panels E and Panel F: Wild-type, bax$^{-/-}$bak$^{-/-}$, parp-1$^{-/-}$, and Clone HP17 (bax$^{-/-}$bak$^{-/-}$, shARP-1) MEFs were treated with MNNG (0.5 mM) alone or together with PARP inhibitor DHIQ, or in the presence of staurosporine (STS). 24 h later cells were photographed under a phase-contrast filter (Panel E), and cell survival was determined by PI exclusion (Panel F). Panel G: Wild-type, bak$^{-/-}$bak$^{-/-}$, parp-1$^{-/-}$, and Clone HP17 MEFs were treated with MNNG (0.25 mM). Cell survival was measured over time by PI exclusion.

FIG. 4, Panels A-C show PARP-mediated cell death is necrotic. Panel A: Wild-type and bax$^{-/-}$bak$^{-/-}$ cells were treated with 0.5 mM MNNG, or 2 µM staurosporine (STS). Transmission electron microscopy was performed 9 h later. Panel B: Transformed wild-type baby mouse kidney (BMK) cells were treated with MNNG alone or together with DPQ. Immunofluorescence was performed 6 h later using an antibody against cytochrome c. Cells were counter-stained with DAPI to show the nuclear morphology. Panel C: Wild-type and $bax^{-/-} bak^{-/-}$ MEFs were treated with indicated agents. Cells were lysed after 8 h. 20 μg of protein was separated on a 4-12% gradient NuPAGE gel. PARP and Lamin B1 were detected using respective antibodies.

FIG. 6, Panels A-E show vegetative cells are more resistant to PARP-mediated necrosis. Panel A: IL-3-dependent hematopoietic $bax^{-/-}bak^{-/-}$ cells were cultured in media with or without IL-3 for 2 d. Cells were treated with MNNG for 15 min at indicated concentrations and cell survival was measured by PI exclusion 24 h later. Panel B: Wild-type and $bax^{-/-}bak^{-/-}$ MEFs were plated at $2\times10^4$/well (subconfluent) or $2\times10^5$/well (confluent) in 12-well plates. Cells were cultured for 36 h. Confluent cells were then cultured in the absence of serum for 12 h and subconfluent cells cultured in the presence of serum. Cells were treated with 0.5 mM MNNG for 15 min. Cell survival was determined 24 h later by PI exclusion. Panels C and D: IL-3-dependent $bax^{-/-}bak^{-/-}$ cells were cultured in the presence or absence of IL-3 for 2 d. Cells were then treated with MNNG for 15 min. PARP activity was determined by immunoblotting of PAR, and NAD and ATP levels measured and shown as the percentage of the levels in untreated cells. (Panel C). Cellular NAD pool was decreased in both proliferating and vegetative cells, while cellular ATP pool was preserved in vegetative cells but not in proliferating cells (Panel D). Panel E: PARP activation preferentially depletes cytosolic NAD. IL-3-dependent cells were treated with 0.5 mM MNNG for 15 min. Cells were fractionated and the NAD levels were measured in total cell lysates, as well as in the cytosolic and mitochondrial fractions. Immunoblotting of tubulin and COX IV were performed to assure the purity of the fractionation.

Figure 1:
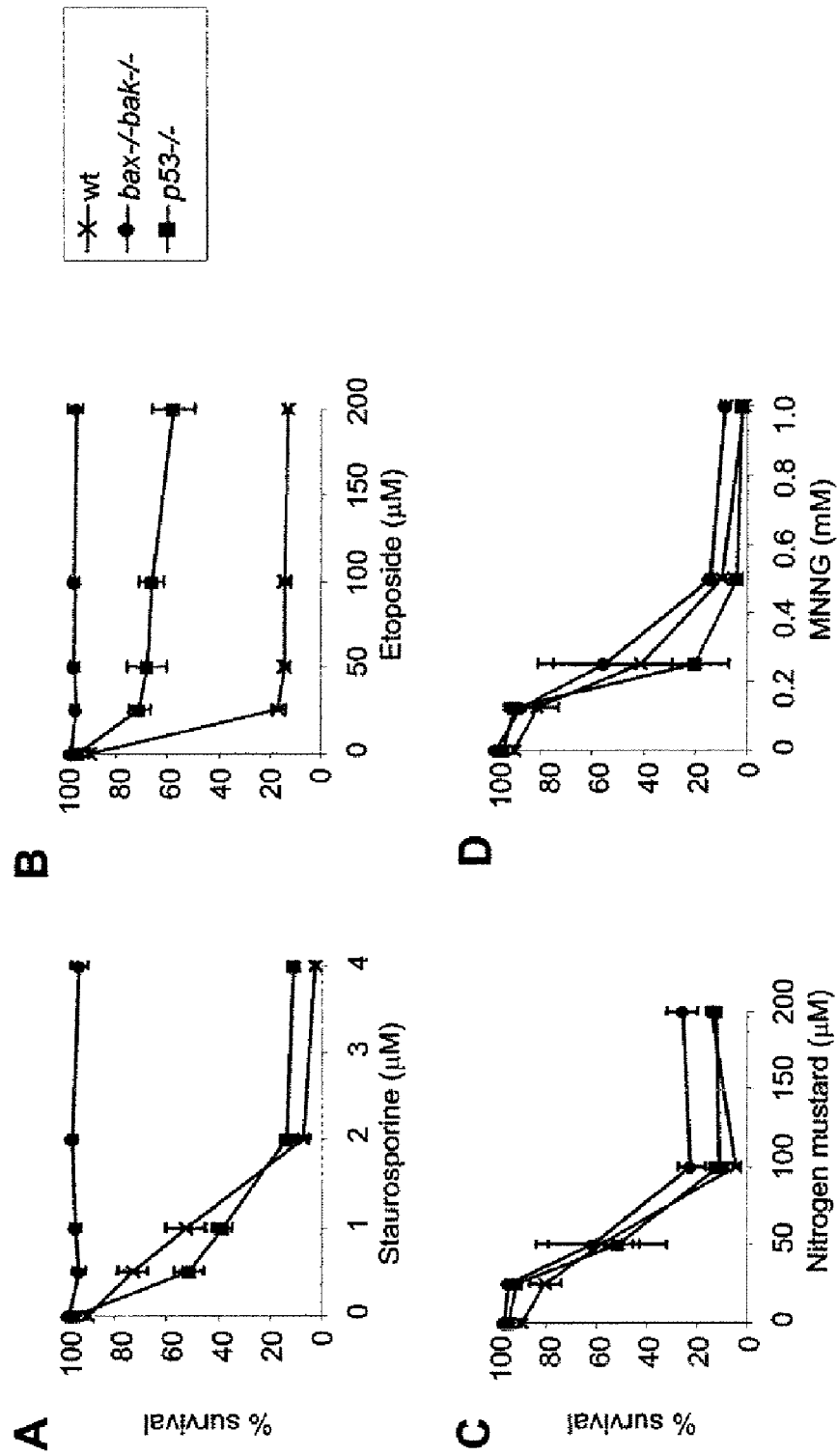
FIG. 1, Panels A-D show that cells deficient in p53 or Bax/Bak are susceptible to DNA alkylating agents. MEFs from wild-type, p53$^{-/-}$, and bax$^{-/-}$bak$^{-/-}$ mice were treated with staurosporine (Panel A), etoposide (Panel B), nitrogen mustard (Panel C), and MNNG (Panel D) as described in Materials and Methods. Drug concentrations were indicated in the individual panels. Cell survival was determined for triplicate samples by PI exclusion at 20 h following treatment. Data is presented as mean+/−S.D., and is representative of three independent experiments.

Panel A, Cellular glycolysis rate in the presence or absence of IL-3. IL-3-dependent $bax^{-/-}bak^{-/-}$ cells were cultured in the presence or absence of IL-3 for 2 d. One million cells were harvested and their glycolysis rate determined. Panel B: Effect of inhibition of oxidative phosphorylation on ATP levels in cells cultured with or without IL-3. Cells cultured in media with or without IL-3 were treated with oligomycin (5 μg/ml) for 30 min. and ATP levels determined. Panel C: IL-3-dependent $bax^{-/-}bak^{-/-}$ cells cultured in the presence or absence of IL-3 for 2 d. An additional population was cultured in the presence of IL-3 in complete medium made without glucose (−glucose), while a fourth population was cultured in the presence of IL-3 and supplemented with 10 mM methyl-pyruvate (+pyruvate) immediate prior to MNNG treatment. Cells were then treated with MNNG and cell survival determined by PI exclusion as described in Materials and Methods. Data presented is representative of 3 independent experiments. Panel D: Methyl-pyruvate (10 mM) was added to the IL-3-dependent wild-type cells immediate prior to MNNG treatment. Cells were treated with MNNG and cell survival determined by PI exclusion.

DETAILED DESCRIPTION OF PREFERRED EMBODIMENTS

Programmed cell death has been defined as cell suicide in response to developmental cues or intrinsic cell stress. The major form of programmed cell death described to date is apoptosis. Apoptotic cell death is ATP-dependent, results in organized proteolytic degradation of the intracellular contents, and phagocytosis of the dying cell without inducing an inflammatory response. Described herein is a form of cell death in which the cell actively initiates its own necrosis in response to DNA damage (e.g. by an alkylation agent). This form of cell death is independent of the major apoptotic effectors (e.g. p53, Bax, Bak, and caspases).

In response to DNA damage, cells activate PARP, an enzyme that catalyzes poly(ADP-ribosyl)ation of a variety of proteins (D'Amours et al. 1999). This activity of PARP can increase the accessibility of DNA to DNA repair enzymes and transcription factors. There has been controversy concerning the role of PARP in the regulation of cell survival/death in response to DNA damage. Some work has implicated PARP in the regulation of DNA repair and cell survival (Wang et al. 1997), while others have implicated PARP in initiating cell death by either apoptosis (Yu et al. 2002) or necrosis (Ha and Snyder 1999). It has been observed that the activation of PARP runs a metabolic test on the damaged cell. In cells that maintain their ATP production exclusively by catabolizing glucose, PARP activation results in a rapid decline in cellular ATP and necrotic death. In contrast, in cells that can maintain non-glucose-dependent oxidative phosphorylation, PARP activation does not compromise cellular bioenergetics and such cells are resistant to DNA damage-induced death. Accordingly, activation of PARP can be used to kill cell, particularly cancer cells, which rely on catabolizing glucose to maintain their ATP production.

The cellular test run by PARP provides a potential explanation for the ability of DNA alkylating drugs to act as effective chemotherapeutic agents. In general it is believed that most chemotherapeutic drugs induce tumor cells to die by apoptosis. However, a central feature of perhaps all cancers is the development of apoptotic resistance. The most common genetic abnormality in human tumors is mutation of p53. Loss of p53 function is associated with pronounced apoptotic resistance (Vousden and Lu 2002; Gudkov and Komarova 2003).

Nevertheless, alkylating agents remain the single most effective and broadly active chemotherapeutic agents (Chabruer and Longo 2001). It is thought that the efficacy of alkylating drugs results from the selective ability to kill proliferating cells. Proliferating cells have been shown to have an increased propensity to apoptosis under some circumstances (Evan and Vousden 2001). However, the discovery that neither Bax/Bak deficiency nor p53 deficiency is required to affect cell death in response to DNA damage suggested that there might be alternative explanations for the ability of alkylating agents to selectively kill tumor cells such as by PARP-mediated necrosis.

Tumor cells display an abnormal propensity for growth and are in net protein and lipid synthesis. As a result, they maintain ATP production almost exclusively through catabolizing glucose through a mixture of glycolysis and oxidative phosphorylation termed aerobic glycolysis (Holt 1983; Baggetto 1992). In contrast, cells that are not actively growing or replicating are capable of catabolizing a variety of metabolic substrates to maintain ATP production (Eaton et al. 1996). Inhibition of mitochondrial respiratory chain has been shown to induce death of vegetative cells (Hartley et al. 1994; Woodgate et al. 1999; Ohgoh et al. 2000). In contrast, mitochondrial inhibitors do not affect the viability of cells with a high level glycolytic rate because they are capable of maintaining ATP levels without mitochondrial respiration (Shchepina et al. 2002). By differentially affecting ATP generation from glycolysis or mitochondrial respiration, activation of PARP can selectively kill cells that are preferentially maintaining their bioenergetics through glycolysis. The proliferating cell's dependency on aerobic glycolysis that determines their sensitivity to PARP-induced cell death. This necrotic form of programmed cell death may be adaptive as it both eliminates the possibility of cell survival and induces an immune response to the dying cell. In response to DNA damage, there is an active redistribution of the macrophage activator HMGB1 from the nucleus to the cytosol. HMGB1 is a small acidic protein localized to chromatin primarily by electrostatic forces (Butler et al. 1985). As histones and other chromatin proteins are modified by poly(ADP-ribosyl)ation, the resulting increase in negative charge may displace HMGB1, thus releasing it from the chromatin. This in turn will increase HMGB1 release into the extracellular environment if the cell loses plasma membrane integrity during necrotic death. In contrast, HMGB1 has been shown to have increased affinity for the DNA fragments created during apoptosis (Scaffidi et al. 2002). This increased sequestration of HMGB1 suppresses its ability to be released from the cell during apoptosis. PARP-dependent release of proinflammatory mediators such as HMGB1 distinguishes programmed necrosis from apoptosis.

The ability of alkylating agent-induced necrosis to induce an inflammatory response to the dying tumor cells may contribute to the efficacy of the drugs as chemotherapeutic agents. Consistent with an important role for PARP-mediated necrosis in inflammatory responses, parp-1$^{-/-}$ mice are resistant to ischemia-reperfusion Eliasson et al. 1997), endotoxic shock (Szabo et al. 1996), and streptozotocin-induced diabetes (Burkart et al. 1999; Masutani et al. 1999, Pieper et al. 1999a).

Thus, necrosis can be a regulated cell fate independent of apoptosis. Necrotic cell death following DNA damage occurs selectively in cells committed to growth. This prevents the survival of cells at risk of accumulating mutations as a result of DNA replication prior to DNA repair. In addition, this form of programmed necrosis induces an inflammatory response that provides additional protection against the accumulation of damaged or aberrant cells, and initiates the repair of the damaged tissue.

Accordingly, the present invention arises out of the discovery that the activation of poly(ADP-ribose) polymerase (PARP) in a tumor cell, an immortalized cell, or a cell committed to growth by the catabolism of glucose leads to cell death that is independent of the apoptotic machinery. This discovery can be used to identify test compounds that can activate PARP and thus, can be used as anti-cancer compounds.

The present invention provides methods of detecting or identifying an anti-cancer agent. In some embodiments, the methods comprise contacting a cell with a test compound and measuring PARP activation. The cell that is contacted with the test compound can be any cell including, but not limited to, a tumor cell, an immortalized cell, an undifferentiated cell, and the like.

As used herein, the term "tumor cell" refers to a cell that has been derived from a tumor. The tumor cell can be from a primary tumor or it can be from a tumor that has metastasized. The tumor cell can also be from a tumor cell line. Tumor cell lines are widely available and can be obtained from many companies including, but not limited to, ATCC (American Type Culture Collection, Rockville, Md.).

As used herein, the term "immortalized cell" refers to a cell that does not under normal growth conditions undergo quiescence. An "immortalized cell" can in some embodiments, be a tumor cell. "Immortalized cells" can also be normal cells that have been transformed to become immortal, Examples of cells that can be immortalized include, but not limited to, embryonic fibroblasts, which include mouse embryonic fibroblasts (MEFs). Mouse embryonic fibroblasts undergo what is termed "crisis" that allows them to become immortalized.

As used herein, the term "undifferentiated cell" refers to a cell that can become differentiated or has the ability to become different types of cells depending on its environment and/or signals that the cell receives.

The test compound can be contacted with a cell by an means that is available that puts the compound in contact with the cell. In some embodiments, the test compound is injected into the cell. If the cell is in an in vitro environment (e.g. cell culture) the test compound can be added to the media that the cell is growing in. The test compound can also be tested in vivo by administering the test compound to an animal. The test compound can be administered by any means available including, but not limited to, injection, orally, and the like.

In some embodiments, the methods of the invention comprises contacting a test compound with the cell population under particular conditions and measuring PARP activation in the cells, as an indication of the effect of the test compound. In some embodiments, it is determined if the cells have undergone necrosis and is used as an indication of the effect of the test compound. In some embodiments, the effect of the test compound is compared what occurs in the absence of any test compound.

In some embodiments the methods comprise contacting more than one test compounds, in parallel. In some embodiments, the methods comprises contacting 2, 3, 4, 5, 6, 7, 8, 9, 10, 15, 20, 25, 30, 40, 50, 100, 1000, at least 2, at least 5, at least 10, at least 50, at least 100, or at least 1000 test compounds in parallel. In some embodiments, the present invention is used High Throughput Screening of compounds and complete combinatorial libraries can be assayed, e.g., up to thousands of compounds. Methods of how to perform high throughput screenings are well known in the art. The methods can also be automated such that a robot can perform the experiments. The present invention can be adapted for the screening of large numbers of compounds, such as combinatorial libraries of compounds. Indeed, compositions and methods allowing efficient and simple screening of several compounds in short periods of time are provided. The instant methods can be partially or completely automated, thereby allowing efficient and simultaneous screening of large sets of compounds.

In some embodiments, the method of the present invention comprises the step of contacting a cell in the presence of a test compound. The cells can then be observed to determine if the test compound activates PARP or causes necrosis. A control may be provided in which the cell is not contacted with a test compound. A further control may be provided in which test compound is contacted with cells that either do not express functional PARP or in which PARP is inactivated. If the cells contacted with the test compound activate PARP, cause necrosis, or both then anti-cancer activity is indicated for the test compound.

Positive and negative controls may be performed in which known amounts of test compound and no compound, respectively, are added to the assay. One skilled in the art would have the necessary knowledge to perform the appropriate controls.

The test compound can be any product in isolated form or in mixture with any other material (e.g., any other product(s)). The compound may be defined in terms of structure and/or composition, or it may be undefined. For instance, the compound may be an isolated and structurally-defined product, an isolated product of unknown structure, a mixture of several known and characterized products or an undefined composition comprising one or several products. Examples of such undefined compositions include for instance tissue samples, biological fluids, cell supernatants, vegetal preparations, etc. The test compound may be any organic or inorganic product, including a polypeptide (or a protein or peptide), a nucleic acid, a lipid, a polysaccharide, a chemical product, or any mixture or derivatives thereof. The compounds may be of natural origin or synthetic origin, including libraries of compounds.

In some embodiments, the activity of the test compound(s) is unknown, and the method of this invention is used to identify compounds exhibiting the selected property (e.g., PARP activation or necrosis inducing). However, in some embodiments instances where the activity (or type of activity) of the test compound(s) is known or expected, the method can be used to further characterize the activity (in terms of specificity, efficacy, etc.) and/or to optimize the activity, by assaying derivatives of the test compounds.

The amount (or concentration) of test compound can be adjusted by the user, depending on the type of compound (its toxicity, cell penetration capacity, etc.), the number of cells, the length of incubation period, etc. In some embodiments, the compound can be contacted in the presence of an agent that facilitates penetration or contact with the cells. The test compound is provided, in some embodiments, in solution. Serial dilutions of test compounds may be used in a series of assays. In some embodiments, test compound(s) may be added at concentrations from 0.01 µM to 1M. In some embodiments, a range of final concentrations of a test compound is from 10 µM to 100 µM. One such test compound that is effective to activate PARP activity is a DNA damaging agent that alkylates DNA.

In some embodiments, the method comprises measuring PARP activation in the presence of the test compound. If the test compound is found to be a PARP activator it is indicative that the test compound is an anti-cancer agent. PARP activation can be measured by any means that demonstrates that the activity of the enzyme PARP has been modulated (increased or decreased) in the presence of the test compound. Examples of how to measure PARP activity include measuring an increase of poly(ADP-ribose) polymers (PAR). Other examples of how to measure PARP activity include, but are not limited to, measuring NAD levels and/or ATP levels. In some embodiments, the levels of NAD are depleted in the presence of the test compound. In some embodiments the levels of ATP are depleted in the presence of the test compound. Methods of measuring NAD and/or ATP levels are routine. Methods of measuring the levels of the poly(ADP-ribose) polymers are routine to one of ordinary skill in the art.

In some embodiments, the test compound activates PARP by at least 10%, at least 20%, at least 30%, at least 40%, at least 50%, at least 60%, at least 70%, at least 80%, at least 90%, at least 100%, at least 200%. In some embodiments, the percent activation of PARP is compared PARP activity observed in the absence of the test compound.

As described above, the test compound can be contacted with a variety of cells to determine if it is a PARP activator, necrosis inducing agent, and/or an anti-cancer agent. In some embodiments, the cell that is contacted with the test compound is unable to undergo apoptosis. In some embodiments the cell is deficient in the expression of the Bax gene, Bak gene, or both.

As used herein, the term "deficient in the expression of" refers to the gene or the product of a gene. The term "deficient in the expression of" can refer to status of the gene in the cell. In some embodiments, the cell is null for the gene in that it has no copies of the gene and is, therefore unable to express the gene. In some embodiments, the status of the gene or gene product is that it is mutated such that the gene is not expressed or that the gene product is not functional or has less function than the wild-type gene. Accordingly, a cell that is deficient in the expression of the Bax gene may have no Bax gene or the Bax gene may be mutated so that the fax gene product is not functional or has less function than the wild-type gene.

In some embodiments, the cell that is contacted with the test compound is null for the Bax gene, Bak gene, or both. A non-limited example of a cell that is deficient for the expression of the Bax gene, Bak gene, or both is a mouse embryonic fibroblast that is deficient in bax and bak gene expression (Zang, et al., Genes & Development, 18:1272-1282 (2004)). This cell line (ATCC patent designation number PTA-9386, deposited Jul. 23, 2008) is also described in U.S. Patent Application 20030091982, filed May 15, 2003, which is hereby incorporated by reference. However, any cell can be used that is deficient for the Bax gene, Bak gene, or both.

In some embodiments, the cell that is contacted with the test compound is deficient in p53 gene expression. In some embodiments, a cell that is deficient in p53 gene expression can have the p53 gene deleted or be "null for p53" or the cell can comprise a mutant of p53 that inactivates the function of p53. In some embodiments, the p53 mutant is a dominant negative mutant or a temperature sensitive mutant. In some embodiments, the p53 mutation is mutation inhibits the binding of p53 to mdm2. In some embodiments, the p53 mutation inhibits the formation of a p53 tetramer.

Methods of creating a cell that is deficient in the expression of a particular gene or set of genes are known in the art. Examples include, but are not limited to those described in U.S. Patent Application 20030091982, siRNA, antisense oligonucleotides, and the like.

In some embodiments, the method comprise determining if a cell has undergone necrosis. One of skill in the art can determine if a cell has undergone necrosis by, for example, analyzing the physical characteristics of the cell. Methods of determining if a cell has undergone necrosis are known to those of skill in the art. Examples of how necrosis is determined include, but are not limited to, measuring organelle swelling, intracellular vacuole formation, plasma membrane disintegration, and nuclear degradation without condensation.

In some embodiments, the methods further comprise performing a control assay. In some embodiments, the control assay comprising contacting a cell with a negative or positive control and measuring, including, but not limited to, PARP activation, necrosis, and the like. In some embodiments, the control compound is compared to the test compound. In some embodiments, the control compound is a negative control (e.g. a compound that does not activate PARP, induce necrosis, and/or is not an anti-cancer agent). A negative control can also be the absence of a test compound or the vehicle (e.g. solvent) that the test compound is contacted with the cell. In some embodiments, the control compound is a positive control (e.g. a compound that activates PARP, induces necrosis, and/or is an anti-cancer agent). As discussed, herein, the PARP activation and/or necrosis can be measured in the absence and the presence of the test compound. In some embodiments, the positive control is MNNG.

The present invention also provides methods of treating cancer in an individual. In some embodiments, the methods comprise identifying an anti-cancer agent according to the methods described herein and administering the agent to the individual. In some embodiments, the anti-cancer agent is co-administered with at least one other cancer treatment to the individual. In some embodiments, the other cancer treatment is a tumor apoptosis inducing agent. In some embodiments, apoptosis inducing agent is a bcl-2 inhibitor.

The anti-cancer agent can be administered by any means to the individual. Methods of administration are known to one of skill in the art. For example, the anti-cancer agent can be prepared as a pharmaceutical composition. In some embodiments, the pharmaceutical composition comprises a pharmaceutically acceptable carrier or diluent. In some embodiments, the pharmaceutical compositions are sterile and/or pyrogen free. The pharmaceutical composition comprising the anti-cancer agent and a pharmaceutically acceptable carrier or diluent may be formulated by one having ordinary skill in the art with compositions selected depending upon the chosen mode of administration. Suitable pharmaceutical carriers are described in the most recent edition of Remington's Pharmaceutical Sciences, A. Osol, a standard reference text in this field.

For parenteral administration, the anti-cancer agent can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as a single doses or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions comprising anti-cancer agent may be administered by any means that enables the agent to reach the agent's site of action in the body of a mammal. Because anti-cancer agents may be subject to being digested when administered orally, parenteral administration, i.e., intravenous, subcutaneous, intramuscular, would ordinarily be used to optimize absorption. In addition, the pharmaceutical compositions of the present invention may be injected at a site at or near hyperproliferative growth. For example, administration may be by direct injection into a solid tumor mass or in the tissue directly adjacent thereto. The composition may also be formulated with a pharmaceutically acceptable topical carrier and the formulation may be administered topically as a creme, lotion or ointment for example.

The dosage administered varies depending upon factors such as: pharmacodynamic characteristics; its mode and route of administration; age, health, and weight of the recipient; nature and extent of symptoms; kind of concurrent treatment; and frequency of treatment. Usually, a daily dosage of the anti-cancer agent is an amount effect to activate PARP sufficiently to have an anti-cancer effect. In some embodiments, the dosage can be about 1 µg to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

In some embodiment, the present invention relates to kits for practicing the above described method of identifying and/or detecting compounds that activate PARP, induce necrosis, or can act as anti-cancer agents. Kits according to this aspect of the invention comprises the a first container comprising cells that are to be contacted with test compound, optionally a second container comprising a positive control, and optionally a third container comprising a negative control. Additionally, to practice the above defined method, means are required to measure PARP activation, necrosis, and/or anti-cancer activity. In some embodiments of this aspect of the invention, a fourth container comprising an antibody that detects PARP activation is provided. At least one of the contained components, for example, the antibody, may be conjugated with an agent, which allows its presence to be detected. In the kits of the invention which are useful to practice the methods of identifying compounds that activate PARP, induce necrosis, and/or have anti-cancer activity cells that are deficient in the bax gene, bak gene, or both are provided.

In some embodiments, the kit comprises an instruction manual that directs the user of this kit how to use the kit. In some embodiments, the instruction manual comprises illustrations, diagrams, charts, graphs, or photographs of exemplary results from when a positive and/or negative control is tested for PARP activation. In some embodiments, the kit comprises means for inhibiting the expression or activity of bak gene expression, bax gene expression, or both. In some embodiments, the kit comprises means for inhibiting apoptosis. In some embodiments, the kit comprises at least one oligonucleotide that can be used to inhibit the expression of a gene that is essential for apoptosis, necrosis, or both.

EXAMPLES

Example 1

Alkylating Agents Induce Cell Death Independent of Apoptotic Effectors

Mouse embryo fibroblasts (MEFs) generated from wild-type, $p53^{-/-}$, and $bax^{-/-}bak^{-/-}$ animals were tested for sensitivity to the alkylating agents mechlorethamine hydrochloride (nitrogen mustard) and N-methyl-N'-nitro-N-nitrosoguanidine (MNNG), as well as to the kinase inhibitor staurosporine and the DNA topoisomerase inhibitor etoposide. Staurosporine induced cell death in wild-type and $p53^{-/-}$ cells, but not in $bax^{-/-}bak^{-/-}$ cells FIG. 1, Panel A). Both $bax^{-/-}bak^{-/-}$ and $p53^{-/-}$ cells were resistant to etoposide treatment (FIG. 1, Panel B). In contrast, both $bax^{-/-}bak^{-/-}$ and $p53^{-/-}$ cells were as sensitive as wild-type cells to nitrogen mustard and MNNG (FIG. 1, Panels C and D). These findings indicate that DNA alkylation initiates cell death in a manner that is independent of the apoptotic initiator p53 or Bax/Bak. Additional experiments confirmed that neither overexpression of the anti-apoptotic protein Bcl-$x_L$ nor addition of the caspase inhibitors zVAD and BAF could inhibit cell death induced by MNNG (data not shown).

Example 2

Activation of PARP and Depletion of NAD and ATP in Response to DNA Damage

Figure 2:
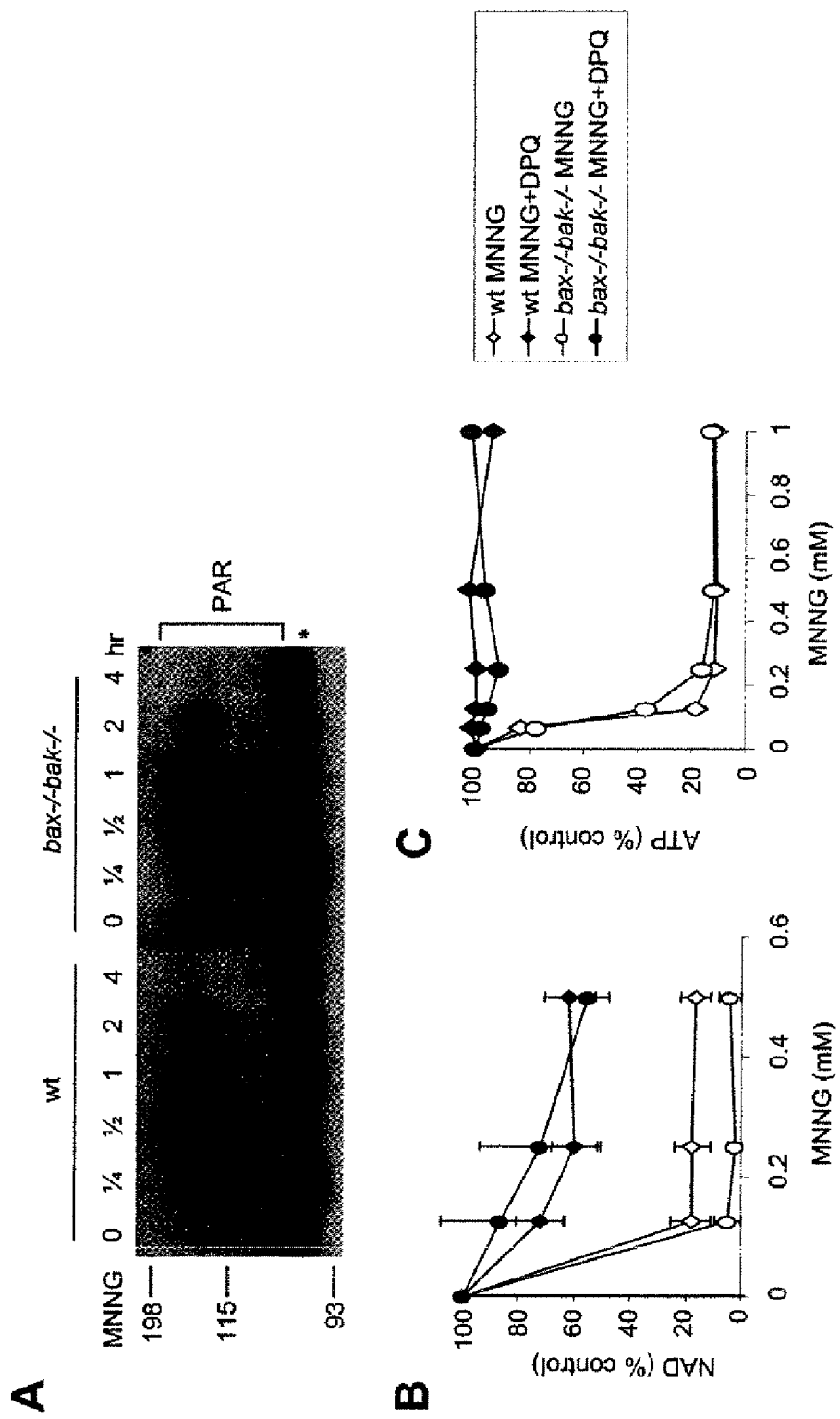
FIG. 2, Panels A-C show that alkylating DNA damage results in PARP activation and bioenergetic collapse. Panel A: MNNG activates PARP in both wild-type and bax$^{-/-}$bak$^{-/-}$ cells. Wild-type and bax$^{-/-}$bak$^{-/-}$ MEFs were treated with MNNG (0.5 mM) for the indicated periods of time. Cells were lysed and immunoblotting was performed using an antibody against poly(ADP-ribose) (PAR). Asterisk marks a non-specific band. Panels B and C: Depletion of NAD and ATP in response to PARP activation. Wild-type and bax$^{-/-}$bak$^{-/-}$ cells were treated with MNNG at indicated concentrations for 30 min, alone or together with PARP inhibitor DPQ. The cellular NAD (Panel B) and ATP (Panel C) levels were determined. Concentrations of NAD and ATP were normalized with that of untreated cells.

DNA alkylation has been shown to activate the enzymatic activity of PARP, which catalyzes the synthesis of poly(ADP-ribose) polymers on histones and other chromatin-associated proteins in the vicinity of the DNA adduct (D'Amours et al. 1999). This process promotes the efficient recognition of the DNA damage by DNA repair enzymes. Because β-nicotinamide adenine dinucleotide (NAD) is the substrate for poly(ADP-ribosyl)ation, PARP activation has been shown to deplete cellular NAD and contribute to cell death in response to excitotoxic stimuli or reperfusion injury (Szabo and Dawson 1998; Pieper et al. 1999b). We tested whether PARP activation is involved in death of $bax^{-/-}bak^{-/-}$ cells in response to DNA damage. Upon MNNG treatment, PARP was activated equally in wild-type and $bax^{-/-}bak^{-/-}$ cells, as indicated by the increase of poly(ADP-ribose) polymers (PAR) (FIG. 2, Panel A). MNNG treatment also caused a dose-dependent decrease in NAD and ATP in both wild-type and $bax^{-/-}bak^{-/-}$ cells. This depletion could be prevented by nicotinic acid analogue DPQ which among other functions acts in vitro as a PARP inhibitor (FIG. 2, Panels B and C).

Example 3

DNA Damage-induced Necrosis is PARP-dependent

The above findings suggest that DNA alkylating agents can trigger the PARP-dependent depletion of NAD and ATP in cells, and this process is independent of the mitochondrial apoptosis pathway. To test directly if PARE is required to initiate NAD/ATP depletion and cell death in response to NG, shRNA was used to suppress the expression of PARP-1, which accounts for 90% of the PARP activity among the PARP family members (Smith 2001). Among the stable $bax^{-/-}bak^{-/-}$ MEF clones transfected with an shRNA vector, Clone HP17 demonstrated a dramatic reduction of PARP-1 expression, while in Clone HP11 the PARP-1 level was moderately decreased (FIG. 3, Panel A). Correlating with the levels of PARP-1 expression, poly(ADP-ribosyl)ation was moderately decreased in clone HP11 upon MNNG treatment, and significantly decreased in clone HP17 (FIG. 3, Panel B). The remaining poly(ADP-ribosyl)ation may result from minimal residual PARP-1 which could not be detected by immunoblotting, or from the activation of other PARP family members (Smith 2001). Despite the residual PARP activity in Clone HP17, ATP levels were maintained upon MNNG treatment (FIG. 3, Panel C). Importantly, no cell death was observed in clone HP17 when treated with MNNG at concentrations that killed all vector control $bax^{-/-}bak^{-/-}$ cells (FIG. 3, Panel D).

In contrast to $bax^{-/-}bak^{-/-}$ cells, the death of wild-type cells was only partially rescued by PARP inhibitor DHIQ, suggesting that DNA alkylators can induce more than one death pathway. To test this further, wild-type, $bax^{-/-}bak^{-/-}$, $parp-1^{-/-}$ (Wang et al. 1995), and Clone HP17 ($bax^{-/-}bak^{-/-}$, shPARP-1) cells were compared side by side for sensitivity to different death stimuli (FIG. 3, Panels E and F). All wild-type and $bax^{-/-}bak^{-/-}$ cells died within 20 hours following 0.5 mM MNNG treatment. In contrast, only 30% of similarly treated $parp-1^{-/-}$ cells died and HP17 cells showed essentially no cell death (FIG. 3, Panels E and F). The reduced cell density observed resulted from the growth arrest effect caused by DNA alkylation. Wild-type and $parp-1^{-/-}$ cells were killed by staurosporine, while no cell death was observed in $bax^{-/-}bak^{-/-}$ and clone HP17 cells (FIG. 3, Panel F). The PARP inhibitor DHIQ blocked the cell death partially in wild-type cells, and fully in $bax^{-/-}bak^{-/-}$ cells. DHIQ did not affect the cell death rate in $parp-1^{-/-}$ cells (FIG. 3, Panel F). While additional MNNG-treated $parp-1^{-/-}$ cells underwent apoptosis over the next several days in culture, over 30% of cells treated with 0.25 mM MNNG were alive three days after the treatment, and almost 90% of HP17 cells remained viable (FIG. 3, Panel G). Taken together, these findings indicate that two independently regulated death pathways can be triggered in response to alkylating DNA damage. One is mediated via the Bax/Bak mitochondrial gateway accounting for the cell death observed in $parp-1^{-/-}$ cells and the DHIQ-insensitive death in the other cells. The other form of death is mediated by PARP activation and is Bax/Bak-independent.

Example 4

Cell Death in the Absence of Bax and Bak is Necrotic

To test if PARP-dependent cell death in response to DNA alkylating agents was distinguishable from apoptosis, morphologic features of the cell death in response to MNNG and staurosporine were characterized by electron microscopy. Both wild-type and $bax^{-/-}bak^{-/-}$ cells acquired morphologic changes characteristic of necrosis upon MNNG treatment. These included organelle swelling, intracellular vacuole formation, plasma membrane disintegration, and nuclear degradation without condensation FIG. 4, Panel A). In addition, some wild-type cells displayed an intermediate morphology with both apoptotic and necrotic features. In contrast, staurosporine induced apoptotic morphological changes in wild-type cells including condensed chromatin and no obvious disintegration of the cell body. Although staurosporine treatment induced some non-specific changes in the appearance of $bax^{-/-}bak^{-/-}$ cells, apoptotic features were not observed and the cells remained viable (FIG. 4, Panel A).

A central event in apoptosis is the release of apoptogenic factors such as cytochrome c from the mitochondrial intermembrane space into the cytosol. In $bax^{-/-}bak^{-/-}$ cells treated with MNNG, no change of cytochrome c distribution pattern was observed, although the cells had undergone cell death as indicated by shrinkage of nuclei (FIG. 4, Panel B). In addition, $bax^{-/-}bak^{-/-}$ cells displayed none of the biochemical apoptotic hallmarks tested, including caspase cleavage of PARP-1 and lamin B1 (FIG. 4, Panel C). It is interesting to note that in wild-type cells, treatment with MNNG resulted in some cells acquiring apoptotic features. Cytochrome c release was observed in some cells (FIG. 4, Panel B), and a decrease in the caspase substrates cleavage of PARP-1 and lamin B1 observed in the population as a whole (FIG. 4, Panel C). Furthermore the caspase cleaved forms of PARP-1 and lamin B1 were observed in the wild-type population primarily in the presence of PARP inhibitors (FIG. 4, Panel C). This indicated that MNNG may trigger both necrotic and apoptotic responses in wild-type cells. The apoptotic component of the death is not dependent on PARP, since the apoptotic features persisted when PARP inhibitors DHIQ and DPQ were applied (FIG. 4, Panels B and C).

Example 5

PARP-mediated Cell Death is Proinflammatory

Figure 5:
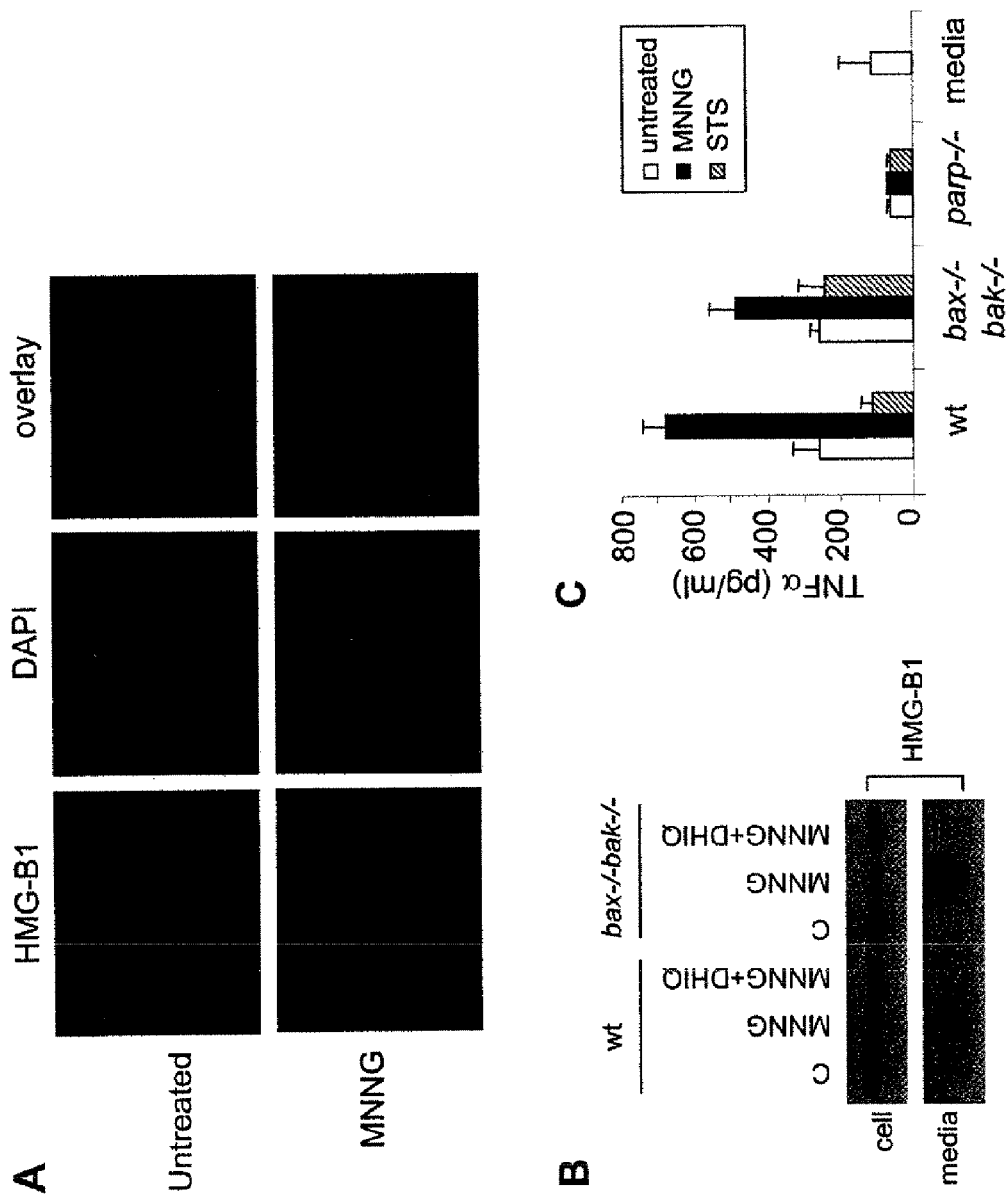
FIG. 5, Panels A-C show PARP-mediated cell death is pro-inflammatory. Panel A: HMGB1 translocates from nucleus into cytosol upon MNNG treatment. $bax^{-/-}bak^{-/-}$ MEFs were treated with 0.5 mM MNNG. 6 h later immunofluorescence was performed using an antibody against HMGB1. Nuclei were visualized by DAPI staining. Panel B: HMGB1 is released into extracellular environment during MNNG-induced necrosis. Wild-type and $bax^{-/-}bak^{-/-}$ MEFs were treated with 0.5 mM MNNG alone or together with DPQ. 16 h later culture media were collected, and cells lysed in RIPA buffer. HMGB1 was detected by immunoblotting in both cell lysates and culture media. Panel C: Inflammatory response triggered by necrosis. Wild-type, $bax^{-/-}bak^{-/-}$, or $parp-1^{-/-}$ MEFs were treated with MNNG (0.5 mM) for 15 min or STS (2 μM) for 2 h. Drugs were washed away and cells refed with fresh media. 20 h later, cell culture media were collected and added to $1\times10^5$ macrophages. Concentration of TNFα was measured 24 h later.

Apoptotic cells die in an ordered fashion, and are engulfed and cleared in vivo, whereas necrotic cells lose their membrane integrity and release the cellular contents into the extracellular environment triggering an acute inflammatory response. One of the proinflammatory molecules reported to be released into the extracellular environment during necrotic cell death is HMGB1, a chromatin-associated protein that if released from cells acts as a ligand for the monocyte/macrophage scavenger receptor RAGE (Scaffidi et al. 2002). MNNG-treated cells were evaluated for HMGB1 localization. In untreated cells, HMGB1 localized to the nucleus. However, 6 hours following treatment of MNNG there was translocation of HMGB1 from nucleus to the cytosol (FIG. 5, Panel A). This redistribution was active, as it began prior to observable cell death. By 16 hours after MNNG treatment, HMGB1 could be found in the extracellular environment. HMGB1 redistribution and release was blocked when PARP was inhibited (FIG. 5, Panel B). To determine if the release of factors such as HMGB1 is sufficient to induce an inflammatory response in innate immune cells, cell culture medium was collected and added to cultured macrophages. Macrophage activation was assessed by the production of the proinflammatory cytokine TNFα. Culture medium from MNNG treated wild-type and ba bak$^{-/-}$ cells induced TNFα production, whereas medium harvested from apoptotic cells (wild-type and parp-1$^{-/-}$ treated with staurosporine) failed to do so (FIG. 5, Panel C). Taken together, these findings indicate that MNNG induces necrotic cell death, and that the dying cell actively establishes its ability to release inflammatory mediators upon death.

Example 6

Proliferating Cells are More Sensitive to PARP-Mediated Necrosis

In vivo, chemotherapeutic agents selectively induce the death of tumor cells and normal cells undergoing cell division (DeVita 1997). We next investigated whether MNNG-induced cell death might account for such selectivity. Since both apoptotic and necrotic death pathways can be activated by DNA damage, we took advantage of bax$^{-/-}$bak$^{-/-}$ cells to study PARP-mediated necrosis without interference from apoptosis. Interleukin-3 (IL-3)-dependent bax$^{-/-}$bak$^{-/-}$ cells were utilized. Upon IL-3 deprivation, these cells withdraw from the cell cycle but remain viable. The bax$^{-/-}$bak$^{-/-}$ cells proliferating in response to IL-3 were killed by MNNG in a dose-dependent manner. In contrast, IL-3-deprived bax$^{-/-}$bak$^{-/-}$ cells were resistant to MNNG (FIG. 6, Panel A). Furthermore, this protection was not transient. When IL-3 was added to the IL-3-dependent cultures 24 hour after 0.5 mM MNNG treatment, cells recovered and cell viability in the culture 48 hours later was reproducibly greater than 85%. In contrast, the viability of cells treated with 0.5 mM MNNG in the presence of IL-3 continued to decline over the first 72 hours after treatment. Similarly, we observed that MEFs grown to confluence and then serum-deprived were less sensitive to MNNG-induced cell death than subconfluent MEFs cultured in the presence of serum (FIG. 6, Panel B). This suggested that growth factor signal transduction and/or cell cycle commitment might contribute to sensitivity to PARP-mediated necrosis. To determine whether the decreased susceptibility of non-proliferating cells to MNNG is due to impaired activation of PARP, PARP activation was determined. Equivalent increases in poly(ADP-ribosyl)ation were observed in vegetative and proliferating cells (FIG. 6, Panel C). Based on assaying isolated DNA for strand breaks, equivalent amounts of DNA damage were observed in cells growing in the presence or absence of IL-3. Consistent with the increase of poly(ADP-ribosyl)ation, cellular NAD level was decreased to a similar extent under both culture conditions (FIG. 6, Panel D). However, while the total cellular ATP level was drastically decreased in cells cultured in the presence of IL-3, the ATP level was preserved in the cells deprived of IL-3 ($p<0.01$, FIG. 6, Panel D).

Two major ATP generation mechanisms exist in a cell involving NAD utilization: one through glycolysis using cytosolic NAD as a substrate, and another by mitochondrial oxidative phosphorylation via the $F_1F_0$-ATP synthase. Thus, NAD consumption by PARP would be predicted to have a differential effect on glycolysis and oxidative phosphorylation since cytosolic NAD and mitochondrial NAT) do not exchange with each other. Consistent with this, subcellular fractionation showed that while MNNG treatment reduced cytosolic NAD to minimal levels, mitochondrial NAD was not significantly affected (FIG. 6, Panel E).

Example 7

PARP-Mediated Necrosis is Controlled by Cellular Metabolic Status

Figure 7:
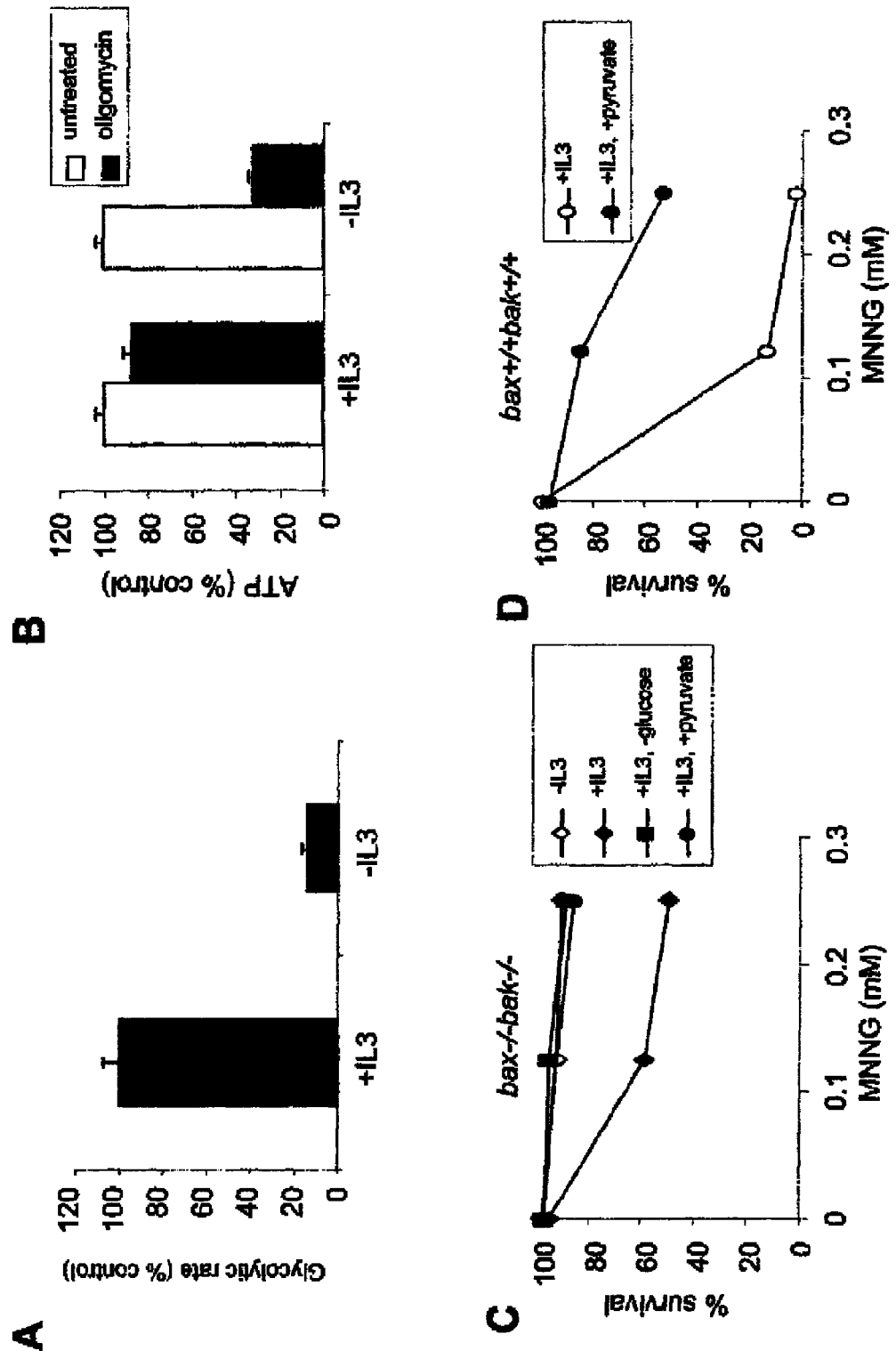
FIG. 7, Panels A-D show susceptibility to PARP-mediated necrosis is controlled by cellular metabolic status.

The cytosolic and mitochondrial NAT pools are used in different pathways to generate ATP, namely glycolysis and oxidative phosphorylation, respectively. The finding that PARP preferentially depletes cytosolic NAD suggested that cells sensitive to PARP might depend on glucose metabolism for ATP production. Consistent with this model, IL-3 treated cells were found to be highly glycolytic (FIG. 7, Panel A) and inhibition of oxidative phosphorylation did not affect the ATP level of these cells (FIG. 7, Panel B). In contrast, IL3-deprived cells displayed a low glycolytic rate (FIG. 7, Panel A, Gonin-Giraud et al. 2002) and ATP levels fell dramatically when oxidative phosphorylation was inhibited with oligomycin (FIG. 7, Panel B). Together, these data suggest that grow factor status affects glycolytic rate and the predominant means of ATP production.

In IL-3-stimulated cells ATP falls when cytosolic NAT) is depleted (FIG. 6, Panel D). This suggests that these cells are unable to increase oxidative phosphorylation to maintain ATP when NAD depletion compromises the ability to carry out glycolysis. A potential explanation for this is that in response to IL-3-induced growth, cells shunt amino acids and lipids away from ATP-generating oxidative metabolism and into synthetic pathways. Under conditions of declining extracellular glucose availability, IL-3-stimulated cells can upregulate mitochondrial fatty acid oxidation to generate ATP, a process not dependent on cytosolic NAD. To determine whether this might have a protective effect, we withdrew IL-3-treated cells from glucose over 48 hours before treatment with MNNG. When IL-3 stimulated cells were adapted to low glucose, they displayed resistance to MNNG-induced death that was comparable to that of IL-3-deprived cells (FIG. 7, Panel C). Thus IL-3 signal transduction alone is not sufficient to confer sensitivity to MNNG-induced cell death.

Finally, to determine if PARP-induced death occurs as a result of glycolytic blockade, we tested whether PARP-induced necrosis could be suppressed by supplying the cells with the glycolytic end product pyruvate. $bax^{-/-}bak^{-/-}$ cells growing in the presence of IL-3 were supplemented with 10 mM methyl-pyruvate, a membrane permeable form of pyruvate, and then treated with MNNG. Methyl-pyruvate supplementation rendered IL-3-stimulated $bax^{-/-}bak^{-/-}$ cells as resistant to MNNG-induced cell death as IL-3-deprived cells (FIG. 7, Panel C). Thus, cells utilizing substrates that are catabolized in the mitochondria to maintain ATP production are resistant to MNNG-induced necrosis. To demonstrate that the resistance to MNNG-induced necrosis was not a peculiar event in $bax^{-/-}bak^{-/-}$ cells, cells with wild-type Bax and Bak were pre-incubated with methyl-pyruvate before MNNG treatment. Similar to $bax^{-/-}bak^{-/-}$ cells, methyl-pyruvate treatment of cells with wild-type Bax and Bak also increased their resistance to MNNG-induced cell death (FIG. 7, Panel D). Thus, cellular metabolic status does not only determine the cell fate in Bax/Bak null background, but also contributes to the regulation of cell fate in cells capable of undergoing Bax/Bak-dependent apoptosis in response to DNA damage.

Example 9

Materials and Methods

Cell Culture and Cell Death Assay

MEFs and BMK cells were cultured as described (Zong et al. 2001; Degenhardt et al. 2002a). IL-3dependent $bax^{-/-}bak^{-/-}$ cells were cultured in RPMI 1640 supplemented with 10% FBS, 2 mM glutamine, 1% penicillin/streptomycin, 20 mM HEPES, 50 μM 2-mercaptoethanol, supplemented with 4 ng/ml recombinant mouse IL-3 (BD-Pharmingen). IL-3 dependent FL5.12 cells were cultured in the same media as used for $bax^{-/-}bak^{-/-}$ cells, supplemented with 0.4 ng/ml recombinant mouse IL-3. To induce cell death with MNNG (Sigma), cells were treated with MNNG for 15 min. Cells were washed and fed with fresh medium with no MNNG, and cultured for indicated periods of time. For etoposide (Calbiochem), staurosporine (Sigma), and mechlorethanmine hydrochloride (nitrogen mustard, Sigma) treatment, the agents remained in the medium. PARP inhibitors DPQ or DHIQ (Sigma) were kept in the medium throughout the course of experiment when used. At the end of experiments, propidium iodide (PI, 1 μg/ml, Molecular Probes) was added to the cells. Cell death was determined using flow cytometry by PI exclusion.

Immunoblotting and Immunofluorescence

Cells were lysed in RIPA buffer (1% Sodium Deoxycholine, 0.1% SDS, 1% Triton X-100, 10 mM Tris pH8.0, 0.14 M NaCl) with protease inhibitor complex (Roche). 20 μg of protein was loaded on pre-cast 4-12% NuPAGE gel. Western blotting was performed with the following antibodies: PARP (clone C2-10, BD-Pharmingen or Trevigen), Lamin B1 (M-20, Santa Cruz), Tom20 (FL-145, Santa Cruz), PAR (BD-Pharmingen), COX IV (Molecular Probes), Tubulin (Sigma), and HMGB1 (BD-Pharmingen). For immunofluorescence, cells were fixed in 4% paraformaldehyde and permeabilized for 10 min in PBS containing 0.2% Triton X-100. Cells were washed with PBS containing 0.02% Triton X-100 and 1.5% FBS, followed by incubation with antibodies against Bax (6A7, BD-Pharmingen), cytochrome c (BD-Pharmingen), or HMGB1 for 1 h at room temperature. Cells were incubated with Rhodamine-conjugated secondary antibody (Jackson ImmunoResearch). Nuclei were visualized by staining with 1 μg/ml DAPI. Images were captured on a 510 LSM confocal microscope (Zeiss).

Determination of NAD and ATP

The concentration of NAD was measured as described (Jacobson and Jacobson 1976) with modification. Briefly, $1 \times 10^5$ cells were trypsinized and resuspended in 100 μl 0.5 M perchloric acid. Cell extracts were neutralized with equal volume of 1 M KOH and 0.33 M $KH_2PO_4/K_2HPO_4$ pH 7.5. After centrifugation to remove the $KClO_4$ precipitate, 200 μl of NAD reaction mixture (600 mM ethanol, 0.5 mM 3-[4,5 dimethylthiazol-2-yl]-2,5 diphenyltetrazolium bromide (MTT), 2 mM phenazine ethosulfate, 5 mM EDTA, 1 mg/ml BSA, 120 mM bicine, pH 7.8) was added to 50 μl of the supernatant or NAD standard and incubated at 37° C. for 5 min. 25 μl of alcohol dehydrogenase (0.5 mg/ml in 100 mM bicine, pH7.8) was added to the reaction and incubated at 37° C. for 20 min. 250 μl of 12 mM iodoacetate was added to stop the reaction, and OD was read at 570 nm wavelength. Protein concentration was determined using BCA protein assay reagents (Pierce). The content of NAD was normalized by protein content. For ATP determination, $2 \times 10^4$ cells were lysed in a cell lysis reagent (Catalog #1699709, Boehringer Mannheim). ATP concentration was determined as previously described (Vander Heiden et al. 1999).

Transmission Electronic Microscopy

Cells were rinsed with serum-free DMEM medium, and fixed with pre-warmed 2.5% glutaraldehyde, 2% formaldehyde in 0.1 M sodium cacodylate buffer for 1 h. Cells were washed, post-fixed with 2% osmium tetroxide, dehydrated with ascending grades of ethanol and propylene oxide, and embedded in LX-112 medium (Ladd, Vt.). After polymerization, ultrathin (90 nm) sections were cut with a diamond knife, collected on uncoated copper grids, and stained with uranyl acetate (1%) and lead citrate (0.2%). Samples were examined with a JEOL-1010 electron microscope (JEOL, Japan) operated at 80 KV.

shRNA

A forward oligo with the sequence from a RNA Polymerase III specific U6 promoter CAG TGG AAA GAC GCG CAG GCA (SEQ ID NO:1), and a reverse oligo AAA AAA GGA AGT GAA AGC GGC CAA CGT TCC TCG AGC AAC GTT GGC CGC TTT CAC TTC CG TGT TTC GTC CTT TCC ACA A (SEQ ID NO: 2) that contains a hairpin of the PARP-1 transcript sequence and sequence from the U6 promoter, were used in a PCR to generate a DNA fragment that allows the transcription of the PARP-1 hairpin under the control of the U6 promoter. This DNA cassette was cloned into a pBabe-puro based retroviral vector. The control vector or PARP-1 hairpin constructs were transfected into MEFs using Lipofectamine 2000 transfection reagent (Invitrogen). Single cell clones were propagated using limited dilution, and screened for their PARP-1 expression.

TNFα Measurement

Mouse bone marrow derived macrophages were generated as described (Myung et al. 2000). $5 \times 10^5$ MEFs were plated in 6-well plates, and treated with MNNG for 15 min or staurosporine for 2 h. Cells were washed and refed with 1 ml fresh culture media. 16 h later the cell culture media were collected and added to $1 \times 10^5$ macrophages/well plated in 96-well plates a day earlier. TNFα production was measured 24 h later using a Quantikine TNFα ELISA kit (R&D Systems).

Subcellular Fractionation

IL-3-dependent cells were suspended in hypotonic Buffer A (250 mM sucrose, 20 mM Hepes (pH7.5), 10 mM KCl, 1.5 mM $MgCl_2$, 1 mM EDTA, 1 mM EGTA, 1×protease inhibitor complex (Roche)). Subcellular fractionation was carried out as previously described (Zong et al. 2003). The resulting cytosolic fraction was used directly for NAD measurement, protein quantification, and immunoblotting. The mitochondrial pellet was divided into two equal parts, one vas lysed in 0.5 mM $HClO_4$, and used for NAD measurement, and another part was lysed in RIPA buffer for protein quantification and immunoblotting.

Measurement of Glycolysis

Cellular glycolysis rate was determined as described (Liang et al. 1997) with modifications. One million cells were incubated with 10 μCi 5-$^3$H-glucose PerkinElmer Life Sciences) at 37° C. for 1 h. Following incubation, the reaction was stopped with 0.2 N HCl and $^3H_2O$ was separated from 5-$^3$H-glucose by diffusion in an airtight container. Diffused and undiffused tritium was measured using a 1450 Microbeta scintillation counter (Wallac) and compared to controls of 5-$^3$H-glucose only and $^3H_2O$ only to determine the rate of glycolysis.

REFERENCES

Adams, J. M. 2003. Ways of dying: multiple pathways to apoptosis. Genes Dev 17: 2481-95.

Baggetto, L. G. 1992. Deviant energetic metabolism of glycolytic cancer cells, Biochimie 74: 959-74.

Burkart, V., Z. Q. Wang, J. Radons, B. Heller, Z. Herceg, L. Stingl, E. F. Wagner, and H. Kolb. 1999. Mice lacking the poly(ADP-ribose) polymerase gene are resistant to pancreatic beta-cell destruction and diabetes development induced by streptozocin. Nat Med 5: 314-9.

Butler, A. P., J. K. Mardian, and D. E. Olins. 1985. Nonhistone chromosomal protein HMG 1 interactions with DNA. Fluorescence and thermal denaturation studies. J Biol Chem 260: 10613-20.

Chabruer, B. A. and D. L. Longo. 2001. Cancer Chemotherapy and Biotherapy: Principles and Practices. In. Lippincott Williams and Wilkins, Philadelphia.

Cheng, E. H., M. C. Wei, S. Weiler, R. A. Flavell, T. W. Mak, T. Lindsten, and S. J. Korsmeyer. 2001. BCL-2, BCL-X(L) sequester BH3 domain-only molecules preventing BAX- and BAK-mediated mitochondrial apoptosis. Mol Cell 8: 705-11.

D'Amours, D., S. Desnoyers, I. D'Silva, and G. G. Poirier. 1999. Poly(ADP-ribosyl)ation reactions in the regulation of nuclear functions. Biochem J 342 (Pt 2): 249-68.

Degenhardt, K., G. Chen, T. Lindsten, and E. White. 2002a. BAX and BAK mediate p53-independent suppression of tumorigenesis. Cancer Cell 2: 193-203.

Degenhardt, K., R. Sundararajan, T. Lindsten, C. Thompson, and E. White. 2002b. Bax and Bak independently promote cytochrome C release from mitochondria. J Biol Chem 277: 14127-34.

DeVita, V. T. 1997. Principles of Cancer Management: Chemotherapy. In Cancer: Principles and Practice of Oncology (ed. V. T. DeVita, S. Hellman, and S. A. Rosenberg), pp. 333-347. Lippincott-Raven, Philadelphia.

Eaton, S., K. Bartlett, and M. Pourfarzam. 1996. Mammalian mitochondrial beta-oxidation. Biochem J 320 (Pt 2): 345-57.

Eliasson, M. J., K. Sampei, A. S. Mandir, P. D. Hurn, R. J. Traystman, J. Bao, A. Pieper, Z. Q. Wang, T. M. Dawson, S. H. Snyder, and V. L. Dawson. 1997. Poly(ADP-ribose) polymerase gene disruption renders mice resistant to cerebral ischemia. Nat Med 3: 1089-95.

Evan, G. I. and K. H. Vousden. 2001. Proliferation, cell cycle and apoptosis in cancer. Nature 411: 342-8.

Gonin-Giraud, S., A. L. Mathieu, S. Diocou, M. Tomkowiak, G. Delorme, and J. Marvel. 2002. Decreased glycolytic metabolism contributes to but is not the inducer of apoptosis following IL-3-starvation. Cell Death Differ 9: 1147-57.

Gudkov, A. V. and E. A. Komarova. 2003. The role of p53 in determining sensitivity to radiotherapy. Nat Rev Cancer 3: 117-29.

Ha, H. C. and S. H. Snyder. 1999. Poly(ADP-ribose) polymerase is a mediator of necrotic cell death by ATP depletion. Proc Natl Acad Sci USA 96: 13978-82.

Hartley, A., J. M. Stone, C. Heron, J. M. Cooper, and A. H. Schapira. 1994, Complex I inhibitors induce dose-dependent apoptosis in PC12 cells: relevance to Parkinson's disease. J Neurochem 63: 1987-90.

Holt, J. A. 1983. Cancer, a disease of defective glucose metabolism. Med Hypotheses 10: 133-50.

Jacobson, E. L. and M. K. Jacobson. 1976. Pyridine nucleotide levels as a function of growth in normal and transformed 3T3 cells. Arch Biochem Biophys 175: 627-34.

Kanduc, D., A. Mittelman, R. Serpico, E. Sinigaglia, A. A. Sinha, C. Natale, R. Santacroce, M. G. Di Corcia, A. Lucchese, L. Dini, P. Pani, S. Santacroce, S. Simone, R. Bucci, and E. Farber. 2002. Cell death: apoptosis versus necrosis (review). Int J Oncol 21: 165-70.

Liang, Y., C. Buettger, D. K. Berner, and F. M. Matschinsky. 1997. Chronic effect of fatty acids on insulin release is not through the alteration of glucose metabolism in a pancreatic beta-cell line (beta HC9). Diabetologia 40: 1018-27.

Lindsten, T., A. J. Ross, A. King, W. X. Zong, J. C. Rathmell, H. A. Shiels, E. Ulrich, K. G. Waymire, P. Mahar, K. Frauwirth, Y. Chen, M. Wei, V. M. Eng, D. M. Adelman, M. C. Simon, A. Ma, J. A. Golden, G. Evan, S. J. Korsmeyer, O. R. MacGregor, and C. B. Thompson. 2000. The combined functions of proapoptotic Bcl-2 family members bak and bax are essential for normal development of multiple tissues. Mol Cell 6: 1389-99.

Lister, T. A. 1991. The management of follicular lymphoma. Ann Oncol 2 Suppl 2: 131-5.

Majno, G. and I. Joris. 1995. Apoptosis, oncosis, and necrosis. An overview of cell death. Am J Pathol 146: 3-15.

Masutani, M., H. Suzuki, N. Kamada, M. Watanabe, O. Ueda, T. Nozaki, K. Jishage, T. Watanabe, T. Sugimoto, H. Nakagama, T. Ochiya, and T. Sugimura. 1999. Poly(ADP-ribose) polymerase gene disruption conferred mice resistant to streptozotocin-induced diabetes. Proc Natl Acad Sci USA 96: 2301-4.

Muller, S., P. Scaffidi, B. Degryse, T. Bonaldi, L. Ronfani, A. Agresti, M. Beltrame, and M. E. Bianchi. 2001. New EMBO members' review: the double lie of HMGB1 chromatin protein: architectural factor and extracellular signal. Embo J 20: 4337-40.

Myung, P. S., J. L. Clements, D. W. White, Z. A. Malik, J. S. Cowdery, L. H. Allen, J. T. Harty, D. J. Kusner, and G. A. Koretzky. 2000. In vitro and in vivo macrophage function can occur independently of SLP-76. Int Immunol 12: 887-97.

Ohgoh, M., H. Shimizu, H. Ogura, and Y. Nishizawa. 2000. Astroglial trophic support and neuronal cell death: influence of cellular energy level on type of cell death induced by mitochondrial toxin in cultured rat cortical neurons. J Neurochem 75: 925-33.

Pieper, A. A., D. J. Brat, D. K. Krug, C. C. Watkins, A. Gupta, S. Blackshaw, A. Verma, Z. Q. Wang, and S. H. Snyder. 1999a Poly(ADP-ribose) polymerase-deficient mice are protected from streptozotocin-induced diabetes. Proc Natl Acad Sci USA 96: 3059-64.

Pieper, A. A., A. Verma, J. Zhang, and S. H. Snyder. 1999b. Poly (ADP-ribose) polymerase, nitric oxide and cell death. Trends Pharmacol Sci 20: 171-81.

Scaffidi, P., T. Misteli, and M. E. Bianchi, 2002. Release of chromatin protein HMGB1 by necrotic cells triggers inflammation. Nature 418: 191-5.

Scorrano, L., S. A. Oakes, J. T. Opferman, F. M. Cheng, M. D. Sorcinelli, T. Pozzan, and S. J. Korsmeyer. 2003. BAX and BAK regulation of endoplasmic reticulum Ca2+: a control point for apoptosis. Science 300: 135-9.

Shchepina, L. A., E. N. Popova, O. Y. Pletjushkina, and B. V. Chernyak. 2002. Respiration and mitochondrial membrane potential are not required for apoptosis and anti-apoptotic action of Bcl-2 in HeLa cells. Biochemistry (Mosc) 67: 222-6.

Smith, S. 2001. The world according to PARP. Trends Biochem Sci 26: 174-9.

Szabo, C. and V. L. Dawson. 1998. Role of poly(ADP-ribose) synthetase in inflammation and ischaemia-reperfusion. Trends Pharmacol Sci 19: 287-98.

Szabo, C., B. Zingarelli, M. O'Connor, and A. L. Salzman. 1996. DNA strand breakage, activation of poly (ADP-ribose) synthetase, and cellular energy depletion are involved in the cytotoxicity of macrophages and smooth muscle cells exposed to peroxynitrite. Proc Natl Acad Sci USA 93: 1753-8.

Tsujimoto, Y., L. R. Finger, J. Yunis, P. C. Nowell, and C. M. Croce. 1984. Cloning of the chromosome breakpoint of neoplastic B cells with the t(14; 18) chromosome translocation. Science 226: 1097-9.

Vander Heiden, M. G., N. S. Chandel, P. T. Schumacker, and C. B. Thompson. 1999. Bcl-xL prevents cell death following growth factor withdrawal by facilitating mitochondrial ATP/ADP exchange. Mol Cell 3: 159-67.

Vousden, K. H. and X. Lu. 2002. Live or let die: the cell's response to p53. Nat Rev Cancer 2: 594-604.

Wang, X. 2001. The expanding role of mitochondria in apoptosis. Genes Dev 15: 2922-33.

Wang, Z. Q., B. Auer, L. Stingl, H. Berghammer, D. Haidacher, M. Schweiger, and E. F. Wagner. 1995. Mice lacking ADPRT and poly(ADP-ribosyl)ation develop normally but are susceptible to skin disease. Genes Dev 9: 509-20.

Wang, Z. Q., L. Stingl, C. Morrison, M. Jantsch, M. Los, K. Schulze-Osthoff, and E. F. Wagner. 1997. PARP is important for genomic stability but dispensable in apoptosis. Genes Dev 11: 2347-58.

Wei, M. C., W. X. Zong, E. H. Cheng, T. Lindsten, V. Panoutsakopoulou, A. J. Ross, K. A. Roth, G. R. MacGregor, C. B. Thompson, and S. J. Korsmeyer. 2001. Proapoptotic BAX and BAK: a requisite gateway to mitochondrial dysfunction and death. Science 292: 727-30.

Woodgate, A., G. MacGibbon, M. Walton, and M. Dragunow. 1999. The toxicity of 6-hydroxydopamine on PC12 and P19 cells. Brain Res Mol Brain Res 69: 84-92.

Yu, S. W., H. Wang, M. F. Poitras, C. Coombs, W. J. Bowers, H. J. Federoff, G. G. Poirier, T. M. Dawson, and V. L. Dawson. 2002. Mediation of poly(ADP-ribose) polymerase-1-dependent cell death by apoptosis-inducing factor. Science 297: 259-63.

Zong, W. X., C. Li, G. Hatzivassiliou, T. Lindsten, Q. C. Yu, J. Yuan, and C. B. Thompson. 2003. Bax and Bak can localize to the endoplasmic reticulum to initiate apoptosis. J Cell Biol 162: 59-69.

Zong, W. X., T. Lindsten, A. J. Ross, G. R. MacGregor, and C. B. Thompson. 2001. BH3-only proteins that bind pro-survival Bcl-2 family members fail to induce apoptosis in the absence of Bax and Bak. Genes Dev 15: 1481-6.

Those skilled in the art will appreciate that numerous changes and modifications may be made to the embodiments of the invention and that such changes and modifications may be made without departing from the spirit of the invention. It is therefore intended that the appended claims cover all such equivalent variations as fall within the true spirit and scope of the invention. Also, it is intended that each of the patents, patent applications, and publications referenced above be incorporated by reference herein.

What is claimed is:

1. A kit for identifying a PARP activator comprising:
   1) a container comprising a plurality of immortalized cells that are apoptosis resistant, wherein said cells are deficient in Bax gene expression and Bak gene expression; and
   2) an instruction manual; and
   3) at least one reagent to detect PARP activation.

2. The kit of claim 1, wherein said reagent to detect PARP activation is a reagent used in measuring PAR polymers, NAD depletion, or ATP depletion.

3. The kit of claim 1, wherein the kit further comprises a positive control, wherein the positive control induces PARP activation or induces necrosis of a plurality of immortalized cells upon contact with said plurality of immortalized cells.

4. A kit for identifying a PARP activator comprising:
   1) a container comprising a plurality of immortalized cells that are apoptosis resistant, wherein said cells are deficient in Bax gene expression and Bak gene expression; and
   2) an instruction manual; and
   3) a positive control, wherein the positive control induces PARP activation or induces necrosis of a plurality of immortalized cells upon contact with said plurality of immortalized cells.

5. The kit of claim 4, wherein the positive control is N-methyl-N'-nitro N-nitrosoguandidine (MNNG).

6. The kit of claim 4 further comprising at least one reagent to detect PARD activation.

7. The kit of claim 6, wherein said reagent to detect PARP activation is a reagent used in measuring PAR polymers, NAD depletion, or ATP depletion.

8. The kit of claim 4 further comprising at least one reagent to detect necrosis.

9. The kit of claim 8, wherein said reagent to detect necrosis is a reagent used in measuring organelle swelling, intracellular vacuole formation, plasma membrane disintegration, or nuclear degradation without condensation.

* * * * *

UNITED STATES PATENT AND TRADEMARK OFFICE
CERTIFICATE OF CORRECTION

| | | |
|---|---|---|
| PATENT NO. | : 7,846,723 B2 | Page 1 of 1 |
| APPLICATION NO. | : 12/211046 | |
| DATED | : December 7, 2010 | |
| INVENTOR(S) | : Craig B Thompson et al. | |

It is certified that error appears in the above-identified patent and that said Letters Patent is hereby corrected as shown below:

Column 22, line 9, claim 6, "to detect PARD activation." should read --to detect PARP activation--.

Signed and Sealed this
Fifth Day of April, 2011

David J. Kappos
*Director of the United States Patent and Trademark Office*